(12) United States Patent
Drevet et al.

(10) Patent No.: US 8,501,193 B1
(45) Date of Patent: Aug. 6, 2013

(54) STABILIZED TAT ANTIGEN AND THE USE THEREOF FOR ANTI-HIV VACCINATION

(75) Inventors: Pascal Drevet, Limours (FR); Evelyne Lajeunesse, Antony (FR); Alain Lecoq, Mennecy (FR); Michel Leonetti, Nozay (FR); André Menez, Magny les Hameaux (FR); Gervaise Moine, Montigny le Bretonneux (FR); Robert Thai, Nozay (FR)

(73) Assignee: Commissariat a l'Energie Atomique, Paris (FR)

( * ) Notice: Subject to any disclaimer, the term of this patent is extended or adjusted under 35 U.S.C. 154(b) by 581 days.

(21) Appl. No.: 10/599,448

(22) PCT Filed: Apr. 1, 2005

(86) PCT No.: PCT/FR2005/000795
§ 371 (c)(1),
(2), (4) Date: Mar. 8, 2007

(87) PCT Pub. No.: WO2005/097179
PCT Pub. Date: Oct. 20, 2005

(30) Foreign Application Priority Data

Apr. 1, 2004 (FR) .................................. 04 03429

(51) Int. Cl.
*A61K 39/21* (2006.01)
*C09F 7/00* (2006.01)

(52) U.S. Cl.
USPC .................. 424/208.1; 530/300; 530/304

(58) Field of Classification Search
None
See application file for complete search history.

(56) References Cited

FOREIGN PATENT DOCUMENTS

| WO | WO 99/02185 A | 1/1999 |
|---|---|---|
| WO | WO 00/61067 A | 10/2000 |
| WO | WO 01/43771 A1 * | 6/2001 |
| WO | WO 01/54719 A | 8/2001 |
| WO | WO 01/82944 A | 11/2001 |
| WO | WO 03/011334 A | 2/2003 |
| WO | WO 03/54006 A | 7/2003 |
| WO | WO 03/057885 A | 7/2003 |
| WO | WO 2004/024173 A | 3/2004 |

OTHER PUBLICATIONS

Marasco, et al. Human anti-HIV-1 tat sFv intrabodies for gene therapy of advanced HIV-1-infection and AIDS. Journal of Immunological Methods. 1999; 231: 223-238.*

Marasco, et al. Human anti-HIV-1 tat sFv intrabodies for gene therapy of advanced HIV-1-infection and AIDS Journal of Immunological Methods. 1999; 231.223-238.*

Sanchez, et al. Formulation strategies for the stabilization of tetanus toxoid in poly(lactide-co-glycolide) microspheres. International Journal of Pharmaceutics. 1999; 185,(2):255-266.*

Xian, et at. Degradation of ICF-I in the adult rat gastrointestinal tract is limited by a specific antiserum or the dietary protein casein. journal of Endocrinology 11 995) 146, 21 5-225.*

Lindblad, E.B. Aluminium compounds for use in vaccines. Immunology and Cell Biology (2004) 82:497-505.*

(Continued)

*Primary Examiner* — Zachariah Lucas
*Assistant Examiner* — Stuart W Snyder
(74) *Attorney, Agent, or Firm* — Alston & Bird LLP

(57) ABSTRACT

The invention relates to a vaccine composition comprising at least one type of anti-HIV vaccine composition containing at least one type of stabilized Tat antigen and to the use thereof for preventing and/or treating a human HIV infection.

29 Claims, 19 Drawing Sheets

OTHER PUBLICATIONS

Hakansson and Caffrey Structural and Dynamic Properties of the HIV-1 Tat Transduction Domain in the Free and Heparin-Bound States. Biochemistry 2003, 42, 8999-9006.*

Lindblad, E.B. Aluminum compounds for use in vaccines. Immunology and Cell Biology (2004) 82:497-505.*

Yamamoto, et al. A novel RNA motif that binds efficiently and specifically to the Tat protein of HIV and inhibits the trans-activation by Tat of transcription in vitro and in vivo. Genes to Cells. 2000; 5: 371-388.*

Chang, et al. HIV-1 Tat protein exits from cells via a leaderless secretory pathway and binds to extracellular matrix-associated heparan sulfate proteoglycans through its basic region. AIDS. 1997; 11:1421-1431.*

Silvera, et al. Outcome of Simian-Human Immunodeficiency Virus Strain 89.6p Challenge following Vaccination of Rhesus Macaques with Human Immunodeficiency Virus Tat Protein. J. Virol. 2002; 76(8): 3800-3809.*

Noonan, et al. Identification of Immunodominant Epitopes in Inactivated Tat-Vaccinated Healthy and HIV-I-Infected Volunteers. Journal of Acquired Immune Deficiency Syndromes. 2003; 33:47-55.*

Simon, P.M. Complex carbohydrates in development as human pharmaceuticals. Exp. Opin. Invest. Drugs. 1994; 3(3): 223-239.*

Frankel, et al. Tat Protein from Human Immunodeficiency Virus Forms a Metal-Linked Dimer. Science. 1998; 240(4848): 70-73.*

Jeang (HIV-1 Tat: Structure and Function, 1996—downloaded from: http://www.hiv.lanl.gov/content/sequence/HIV/COMPENDIUM/1996/Part-III/1.pdf on Nov. 5, 2012.*

Heparin Sodium from Porcine Intestinal Mucosa Sigma Prod. Nos. H3393 and H9399, 1996.*

Chang Hsiao C. et al., "HIV-1 Tat protein exists from cells via a leaderless secretory pathway and binds to extracellular matrix-associated heparin sulfate proteoglycans through its basic region", AIDS, vol. 11, No. 12, 1997, pp. 1421-1431.

Noonan Douglas M et al., "Identification of immunodominant epitopes in inactivated Tat-vaccinated healthy and HIV-1-infected volunteers", Journal of Acquired Immune Deficiency Syndromes (1999), May 1, 2003, vol. 33, No, 1, pp. 47-55.

Pauza C. David et al., "Vaccination with Tat toxoid attenuates disease in simian/HIV-challenged macaques", Proceedings of the National Academy of Sciences of the United States of America, Mar. 28, 2000, vol. 97, No. 7, pp. 3515-3519.

Cafaro A. et al., "Control of SHIV-89.6P-infection of cynomolgus monkeys by HIV-1 Tat protein vaccine" Nature Medicine, Nature Publishing Co., vol. 5, No. 6, Jun. 1999, pp. 643-650.

Albini Adriana et al., "HIV-tat protein as a heparin-binding angiogenic growth factor", Oncogene, vol. 12, No. 2, 1996, pp. 289-297.

Hakansson Susanna et al., Structural and dynamic properties of the HIV-1 tat transduction domain in the free and heparin-bound states, Biochemistry, vol. 42, No. 30, Aug. 5, 2003, pp. 8999-9006.

Watson Keith et al., "Interaction of the transactivating protein HIV-1 tat with sulphated polysaccharides", Biochemical Pharmacology, vol. 57, No. 7, Apr. 1, 1999, pp. 775-783.

Rusnati Marco et al., "The basic domain in HIV-1 Tat protein as a target for polysulfonated heparin-mimicking extracellular Tat antagonists", Journal of Biological Chemistry, vol. 273, No. 26, Jun. 26, 1998, pp. 16027-16037.

Misumi Shogo et al., "$Zn^{2+}$ binding to cysteine-rich domain of extracellular human immunodeficiency virus type 1 Tat protein is associated with Tat protein-induced apoptosis", AIDS Research and Human Retroviruses, vol. 20, No. 3, Mar. 2004, pp. 297-304.

Marchio Serena et al., "Cell surface-associated Tat modulates HIV-1 infection and spreading through a specific interaction with gp120 viral envelope protein", Blood, vol. 105, No. 7, Apr. 2005, pp. 2802-2811.

L. Steinaa, A.M. Serensen, J.O. Nielsen, and J.-E.S. Hansen; "Antibodies to HIV-1 Tat protein inhibits teh replication of virus in culture"; Archives of Virology; Springer-Verlag 1994, Printed in Austria; vol. 139; pp. 263-271.

Todd M. Allen, et al.; "Tat-specific cytotoxic T lymphocytes select for SIV escape variants during resolution of primary viraemia"; Nature; vol. 147; Sep. 21, 2000; pp. 386-390.

Alain Lecoq, et al.; Increasing the humoral immunogenic properties of the HIV-1 Tat protein using a ligand-stabilizing strategy; Vaccine; 2008; vol. 26; pp. 2615-2626.

Sabrina Turbant, et al.; Cynomolgus macaques immunized with two HIV-1 Tat stabilized proteins raise and long-lasting immune responses with a pattern of Th1/Th2 response differing from that in mice; Vaccine; 2009; doi:10.1016/j.vaccine.2009.06.083.

"Effect of a heparin fragment (Hep6000) on HIV VPR and Nef Immunogenicity".

* cited by examiner

STABILIZED TAT ANTIGEN AND THE USE THEREOF FOR ANTI-HIV VACCINATION

FIELD AND BACKGROUND OF THE INVENTION

The present invention relates to a stabilized Tat antigen and to uses thereof for anti-HIV immunization.

Acquired immunodeficiency syndrome (AIDS) is a sexually transmissible disease caused by the human immunodeficiency virus (HIV type 1 (HIV-1) or type 2 (HIV-2)). This disease is constantly progressing and, at present, more than 42 million individuals are infected in the world. For this reason, the development of a vaccine is of the utmost urgency for combating this pandemic.

Numerous vaccine approaches have been developed for close to twenty years, without resulting in the development of an effective vaccine. However, the ever increasing knowledge of the infectious cycle and of the viral proteins responsible for progression to the AIDS stage has opened up the path for the use of novel promising vaccine targets: the HIV regulatory proteins. These proteins, which had originally been neglected, have for a few years been the subject of numerous studies due to their role in viral replication.

Among these proteins, the Tat transcriptional regulator of HIV represents a vaccine target which is particularly advantageous since the absence of progression to the AIDS stage is correlated with the presence of hightiter, anti-Tat antibodies and of specific cytotoxic cells (Zagury et al., J. Hum. Virol., 1998, 1: 282-292; Re et al., J. Clin. Virol., 2001, 21: 81-89; Van Baalen et al., J. Gen. Virol., 1997, 78: 1913-1918).

The Tat gene comprises 2 exons encoding a protein of 99 to 103 amino acids depending on the HIV strains. Exon 1, which encodes the first 72 amino acids, has a complete transactivation activity and comprises 5 domains: (1) the N-terminal domain (positions 1 to 21), which is important for the interaction with cell proteins, (2) the cysteine-rich domain (positions 22 to 37) containing 7 cysteine residues (positions 22, 25, 27, 30, 31, 34 and 37), among which 6 are strongly conserved, which domain is involved in transactivation, (3) the central (core) domain corresponding to positions 38 to 48, also involved in transactivation, (4) the basic domain (positions 49 to 57), which comprises the sequences involved in nuclear localization, transcellular transport and binding to the TAR (Trans-activation response) element of the viral LTR (Long Terminal Repeat), and which is also involved in the binding of Tat to heparin, and (5) the glutaminerich domain (positions 50 to 72). Exon 2, which is variable in size, encodes the C-terminal domain (positions 73 to the C-terminal end) which does not have transactivation activity but contains the RGD motif (arginine-glycine-aspartate; positions 78 to 80), required for Tat binding to integrin receptors.

In addition to the Tat protein of 99 to 103 amino acids, there also exists a truncated Tat protein of 86 amino acids, produced in vitro by generation of a stop codon at position 87, due to the mutation of HIV during passage in cell culture.

It has been shown that the isolated and purified, recombinant or synthetic Tat protein associates in solution so as to form oligomers (dimers and trimers) which are very stable, particularly resistant to denaturation and to reduction (100 mM DTT; Tosi et al., Eur. J. Immunol., 2000, 30: 1120-1126). Thus, Tat preparations are heterogeneous and comprise a mixture of monomers, dimers and trimers (patent application US 2003/0158134). However, the exact nature of the interactions involved in the formation of Tat oligomers is not known; the existence of disulfide bridges involving in particular the cysteine at position 37, or other strong chemical interactions, involving in particular polyvalent cations, preferably divalent cations (zinc, cadmium), has been suggested (Battaglia et al., Biochem. Biophys. Res. Commun., 1994, 201: 701-708; Frankel et al., Science, 1988, 240: 70-73; Huang et al., Biochem. Biophys. Res. Comm., 1996, 227: 615-621; Misumi et al., Aids Research and Human Retroviruses, 2004, 20: 297-304).

Tat is a transcription factor essential to viral replication (Fische et al., Nature, 1986, 320: 367-371), which can both activate latent HIV and deregulate the expression of other cellular genes, since it has the particularity of being released by the infected cells and incorporated into other infected or noninfected cells (transcellular transport: Ensoli at al., J. Virol., 1993, 67: 277-287; Chang at al., Aids, 997, 11: 1421-1431). It has been shown that Tat has toxic effects in vitro. These effects comprise: deregulation of cell signals involved in apoptosis, deregulation of the expression of parts of genes of the immune system, such as the interleukin 2 gene and the interferon-alpha gene, or genes encoding major histocompatibility complex (MHC) class I and class II molecules, and/or the induction of angiogenesis.

The relative role of the various forms of Tat in viral infection has not been elucidated and their role in antiviral immunity has not been studied. In fact, it would appear that Tat oligomers do not have any biological activity since, firstly, the extracellular Tat protein produced from mammalian cells is monomeric and, secondly, inhibition of the transactivating activity of Tat using antibodies, which specifically recognize the various forms of Tat, indicates that only the monomer is capable of entering cells and transactivating the viral LTR (Rice at al., Virology, 1991, 185: 451-454; Tosi et al., mentioned above).

Thus, Tat has numerous biological activities and could play a role both in the viral dissemination and in the pathogenesis: progression to the AIDS stage and AIDS-related pathologies, such as Kaposi's sarcoma.

Consequently, although a nonmodified, biologically active Tat protein is capable of protecting monkeys against HIV-1 infection (Cafaro et al., Nat. Med., 1999, 5: 643-650), the use of a toxic protein cannot be envisaged as an immunogen for human immunization.

For this reason, various approaches have been envisaged for obtaining biologically inactive Tat derivatives which can be used as a vaccine in humans.

The inactivation is mainly related to the elimination of the ability of Tat to transactivate transcription of the viral genome, and then to other activities, such as inhibition of the suppression of T cell proliferation. These studies have resulted in the discovery of biologically inactive derivatives of Tat, obtained by means of:

mutations in the sequence of the Tat gene: (i) deletions of the —$NH_2$ or —COOH ends, or else deletion or substitution of the cysteine residues (international application WO 95/31999), (ii) conservative substitution of all the cysteine residues of the cysteine-rich domain (cysteine→serine; international application WO 03/054006), (iii) substitution of at least two amino acid residues of positions 49 to 72 and/or 73 to 101, in particular of positions 49 to 57 (K51T, R52L, R55L, R57L), of the RGD domain (G79A) or of positions 88 to (K89L, E92Q), and optionally of the cysteine at position 27 (C27S) (international application WO 03/057885), and (iv) deletion of an amino acid residue (C22, T23, N24, Y26, K28/29, C30, C31, F32, K33, E35, F38, K41, Y47, A57) or substitution of an amino acid residue (T23A, N24A, C22G, K41T; international application WO 99/27958), analysis of the Tat gene mutations naturally present in nonprogressive seropositive individuals: variants of the N-terminal region or of exon 2 (international application WO 01/12220); variant derived from the Oyi isolate, having the substitution C22S (international application WO 00/61067), chemical or physical treatments of the Tat protein: (i) treatment with an aldehyde, such as formaldehyde and glutaraldehyde (PCT international application WO 96/27389), (ii) carboxymethylation of cysteines by means of iodoacetic acid or of iodoacetamide (PCT international application WO 99/33872), and (iii) oxidation, in particular with hydrogen peroxide or sodium periodate or else irradiation (patent application US 2003/0215797; international application WO 01/12220; Cohen et al., P.N.A.S., 1999, 96: 10842-10847), and purification of the recombinant Tat protein by means of a method for eliminating the contaminating RNA and endotoxin (PCT international application WO 03/073984).

It has in particular been shown that a Tat derivative in which cysteines 22 and 37 are substituted with serines is immunogenic (Caselli et al., J. Immunol., 1999, 162: 5631-5638) and that a carboxymethyl derivative of Tat is immunogenic and capable of inducing a slowing down of the progression of the disease in monkeys (Pauza et al., P.N.A.S., 2000, 97, 3515-3519).

These results indicate that a Tat immunogene which is biologically active or has been inactivated beforehand can contribute to the setting up an effective HIV vaccine. However, the effectiveness of a vaccine depends to a large extent on its ability to induce a strong immune response. Now, the Tat molecule is known for its immunosuppressive capacities (Cohen et al., mentioned above) and is weakly immunogenic in animals, in particular in monkeys. Thus, the slowing down of the disease induced by the carboxymethylated Tat toxoid requires a series of 5 immunizations (Pauza et al., P.N.A.S., 2000, 97: 3515-3519) and the protection provided by the biologically active Tat molecule has been obtained after a series of 9 or 10 immunizations, according to protocols (Cafaro et al., mentioned above).

Consequently, in order to develop a vaccine which is effective against HIV, there exists a real need to develop a Tat-derived antigen which exhibits increased immunogenicity compared with that of the Tat antigens of the prior art.

The inventors have given themselves the aim of developing such an antigen.

SUMMARY OF THE INVENTION

The inventors have shown, surprisingly, that the Tat protein is very unstable and rapidly degraded by proteolytic enzymes. The demonstration of this characteristic of Tat has led them to put forward the hypothesis that improving the stability of Tat should decrease its proteolytic susceptibility and increase its half-life in the organism, and also its immunogenicity. This hypothesis was validated by comparing the immunogenicity of nonmodified Tat with that of Tat stabilized beforehand, either by formation of a complex with a ligand, or by incorporation of hydrophobic groups. By comparison with nonmodified Tat or a Tat toxoid the cysteines of which are blocked with acetamidomethyl groups which are relatively nonimmunogenic, the stabilized Tat derivatives induce anti-Tat antibody titers which are at least 10 times higher in animals (factor of 10 to 35) and are capable of inducing a Tat-specific cell response. In addition, these derivatives exhibit an impaired transactivating activity indicating an absence of toxicity.

Consequently, a subject of the present invention is an HIV vaccine composition characterized in that it comprises at least one stabilized Tat antigen resistant to proteolytic degradation, said stabilized Tat antigen being selected from the group consisting of:

a) a complex between an HIV Tat protein or a Tat fragment of at least 11 amino acids, and a non-metal ligand of Tat, b) an HIV Tat protein or a Tat fragment of at least amino acids, modified by substitution with a hydrophobic amino acid and/or the modification, with a hydrophobic group, of at least one amino acid of the Tat sequence, with the exclusion of the substitutions R52L, R55L, R57L, R78A, G79A, E80A and K89L, and c) a complex between the Tat protein or the Tat fragment modified by substitution with a hydrophobic amino acid and/or the modification, with a hydrophobic group, of at least one amino acid of the Tat sequence defined in b), and a non-metal ligand of Tat.

The combination of the two modifications in c) advantageously makes it possible to obtain an increase in Tat immunogenicity greater (by at least a factor of five) than that obtained with just one of the modifications, in a) or in b).

DEFINITIONS

The term "Tat antigen" is intended to mean a monomer or an oligomer, in particular a dimer, of a Tat protein or of a fragment of this protein of at least 11 amino acids, capable of inducing a specific humoral and/or cellular response in a human or animal mammal; said Tat antigen is either biologically active, or inactivated by mutation of the sequence of the Tat gene, in particular by substitution, with serine(s), of cysteine residue(s) of the cysteine-rich region, or else by physical treatment (irradiation) or chemical treatment (action of an aldehyde, oxidation) of Tat, as defined above.

The term "Tat oligomer" is intended to mean the association of Tat monomers (protein and/or fragment) which are identical to or different from one another (homo- or heterooligomers), by means of one or more covalent and/or noncovalent bonds. The covalent oligomers result in particular from the formation of disulfide bridge(s) by oxidation of cysteine residues or from the formation of other chemical bond(s) (oxime, hydrazone), or else from reaction with homobifunctional groups such as glutaraldehyde or heterobifunctional groups such as 3-((2-aminoethyl)dithio)propionic hydrochloride. The noncovalent oligomers can be formed by means of leucine-zipper motifs or metal ions, such as zinc or cadmium.

The term "Tat protein" (or "Tat") is intended to mean the Tat protein of any HIV strain (HIV-1 or HIV-2), corresponding to a sequence of approximately 86 to 103 amino acids, depending on the strains.

The term "non-metal ligand of Tat" is intended to mean a compound other than a metal ion, which is capable of binding to Tat or to a Tat fragment; it may be protein, lipid, carbohydrate, nucleotide (DNA, RNA) or mixed (glycolipid, glycoprotein) in nature. It includes in particular: the HIV Vpr protein; polysulfated sugars such as, for example: dextran sulfate, pentosan polysulfate and polysulfated glycosaminoglycans, in particular heparin, heparan sulfate, and the compounds as described in Rusnati et al., J. Biol. Chem. 1998, 273: 16027-16037.

The term "metal ligand of Tat" is intended to mean metal ions, in particular polyvalent cations, preferably divalent cations, such as zinc ($Zn^{2+}$) and cadmium ($Cd^{2+}$).

The term "stabilized Tat antigen" is intended to mean a derivative of the Tat protein or the Tat fragment as defined above, comprising a physical or chemical modification such that, after 2 hours of digestion with chymotrypsin (enzyme/substrate ratio of 1/50 (WW)), the proportion of Tat derivative recognized by an anti-Tat monoclonal antibody directed against the epitope (KGLGISYGRK) of the core region is at least 20% greater, preferably at least 50% greater, than the proportion of nonmodified Tat recognized by the same antibody, subsequent to the same digestion.

The term "hydrophobic amino acid" is intended to mean either a natural amino acid chosen from: L (leucine), V (valine), I (isoleucine), A (alanine), M (methionine), F (phenylalanine), W (tryptophan) or Y (tyrosine), or of a nonproteinogenic amino acid, in which the carbon bearing the R side chain, i.e. the —CHR— group, located between —CO— and —NH— in the natural peptide chain, is replaced with a motif which does not form part of the makeup of a natural protein or a natural peptide. By way of nonlimiting example, mention may be made of norleucine (Nle) and cyclohexaalanine (Cha).

The term "hydrophobic group" is intended to mean an alkyl or an aryl, such as, for example: S-tert-butyl, neopentyl, isobutyl, isopropyl, 1-methylpropyl, benzyl, indoyl or a naphthyl. Said hydrophobic group can be introduced onto the amino acid by means of a reagent of 1-iodo-2,2-dimethylpropane, a-bromotoluene, tert-butyl disulfide or N-tert-butylacrylamide type. The amino acid residues of Tat or of the Tat fragment which are modified with said hydrophobic groups are polar or charged amino acids which can be functionalized. Among these amino acids, mention may be made of those having the following reactive functions: —OH [serine (S), threonine (T) or tyrosine (Y)], —SH [cysteine (C)], —$NH_2$ [lysine (K) or arginine (R)] or —COOH [aspartic acid (D) or glutamic acid (E)].

According to an advantageous embodiment of said vaccine composition, said non-metal ligand of Tat is protein, lipid, carbohydrate, nucleotide or mixed in nature.

According to an advantageous arrangement of this embodiment of said vaccine composition, said non-metal ligand is a polysulfated sugar chosen from: dextran sulfate, pentosan polysulfate and polysulfated glycosaminoglycans such as heparin and heparan sulfate.

Preferably, said Tat/polysulfated sugar complex, for example a Tat/heparin complex, is an equimolar complex.

Preferably, said heparin is a heparin having a molecular weight of 15 000 Da or a heparin fragment having a molecular weight of 6000 Da, which binds to Tat with a high affinity.

According to another advantageous arrangement of this embodiment of said vaccine composition, said non-metal ligand of Tat is the HIV Vpr protein.

According to another advantageous embodiment of said vaccine composition, said Tat protein or said Tat fragment is modified by substitution and/or modification of 1 to 7 cysteines, located at positions 22, 25, 27, 30, 31, 34 and/or 37.

Preferably, said cysteine is modified with an S-tert-butyl group (CysStBu) or substituted with a hydrophobic amino acid selected from the group consisting of: a leucine, a tryptophan and a phenylalanine. Preferably, at least the four cysteines at position 25, 27, 30 and 31 are substituted with a hydrophobic amino acid and/or modified with a hydrophobic group as defined above.

According to yet another advantageous embodiment of said vaccine composition, said stabilized Tat antigen derived from a Tat protein or a Tat fragment which has been inactivated (inactivated Tat antigen), preferably comprising the substitution of each of the cysteines at positions 22, 34 and 37 to serines (TatC(22,34,37)S), or else the substitution of each of the arginines at positions 52 and 53 to glutamines (TatR (52,53)Q). Preferably, it is a Tat antigen in which the cysteines at positions 22, 34 and 37 are substituted to serines and the cysteines at positions 25, 27, 30 and 31 are modified with an S-tert-butyl group or substituted with a leucine, a tryptophan or a phenylalanine. Such an antigen exhibits both a high immunogenic capacity and a lack of toxicity, indicated by an absence of ability to transactivate the viral LTR.

According to yet another advantageous embodiment of said composition, said Tat protein or the fragment of said protein is chosen from: the 101 amino acid Tat protein (Tat101), the 86 amino acid Tat protein (Tat86), the Tat fragment 1 to 57 and fragments of at least 11 amino acids included in the above proteins or fragment, preferably those comprising from 11 to 50 amino acids, preferably those comprising between 11 and 35 amino acids, even more preferably those comprising between 15 and 25 amino acids.

According to yet another advantageous embodiment of said vaccine composition, said stabilized Tat antigen derives from the Tat protein of SEQ ID No. 1 or from a fragment of at least 11 amino acids of this protein.

According to yet another advantageous embodiment of said vaccine composition, said Tat protein or said Tat fragment in a) is also complexed with a metal ligand of Tat chosen from polyvalent cations, preferably divalent cations, such as zinc ($Zn^{2+}$) or cadmium (Ce); the Tat complex in a) thus comprises both a metal ligand and a non-metal ligand.

According to yet another advantageous embodiment of said vaccine composition, said Tat protein or said Tat fragment modified in b) or in c) is also complexed with a metal ligand of Tat chosen from polyvalent cations, preferably divalent cations, such as zinc ($Zn^{2+}$) or cadmium ($Cd^{2+}$); the complexes of Tat modified in b) and in c) thus comprise, respectively, a non-metal ligand, and both a metal ligand and a non-metal ligand.

According to yet another advantageous embodiment of said vaccine composition, said Tat protein or said Tat fragment is a monomer.

According to yet another advantageous embodiment of said vaccine composition, said Tat protein or said Tat fragment is an oligomer formed by the covalent and/or noncovalent association of monomers of Tat (protein(s) and/or fragment(s)); preferably, it is a dimer. The oligomers associated covalently comprise in particular at least one intermolecular disulfide bond involving a cysteine residue of the Tat amino acid sequence, in particular a cysteine of the cysteine-rich region, preferably one of the cysteines at position 22, 34 or 37. In accordance with the invention, at least one of the cysteines which is not involved in a disulfide bridge can be substituted with a hydrophobic group and/or modified with a hydrophobic group as defined above, the residual cysteines being, for example, substituted to an amino acid which does not comprise a sulfhydrile group, such as serine. Alternatively, the oligomers can also be associated noncovalently by means of metal ions such as zinc or cadmium.

According to yet another advantageous embodiment of said vaccine composition, the Tat protein and/or the Tat fragment of the complex in a) or c), or else the Tat protein and/or the Tat fragment modified in b), are in the form of a recombinant vector or polynucleotide encoding said protein and/or said fragment.

The stabilized Tat antigens according to the invention are in particular represented by:

a) a complex between a Tat protein of 101 amino acids (Tat101) or of 86 amino acids (Tat86) and a polysulfated sugar such as dextran sulfate, pentosan polysulfate and heparin, in particular an equimolar complex, for example a complex with a heparin having a molecular weight of 15 000 Da, or a heparin fragment having a molecular weight of 6000 Da, b) a Tat protein of 101 amino acids (Tat 101) or of 86 amino acids (Tat86) comprising a cysteine modified with an S-tert-butyl group at positions 22, 25, 27, 30, 31, 34 and 37, c) a Tat protein of 101 amino acids (Tat101) or of 86 amino acids (Tat86) comprising a serine at positions 22, 34 and 37 and a cysteine modified with an S-tert-butyl group at positions 25, 27, 30 and 31, d) a Tat protein of 101 amino acids (Tat101) or of 86 amino acids (Tat86) comprising a leucine at positions 22, 25, 27, 30, 31, 34 and 37, e) a Tat protein of 101 amino acids (Tat101) or of 86 amino acids (Tat86) comprising a phenylalanine at positions 22, 25, 27, 30, 31, 34 and 37, f) a Tat protein of 101 amino acids (Tat101) or of 86 amino acids (Tat86) comprising a tryptophan at positions 22, 25, 27, 30, 31, 34 and 37, g) a Tat dimer formed from the association, by means of a disulfide bridge between the cysteines at position 34, of two Tat proteins or of two Tat fragments which have been modified, comprising a serine at positions 22 and 37 and a leucine at positions 25, 27, 30 and 31, h) a complex between a Tat protein or a Tat dimer as defined in b), c), d), e), f) or g) and a polysulfated sugar such as dextran sulfate, pentosan polysulfate or heparin, in particular an equimolar complex, for example with a heparin having a molecular weight of 15 000 Da or a heparin fragment having a molecular weight of 6000 Da, and i) a complex between a noncovalent oligomer of Tat proteins of 101 or 86 amino acids and/or of Tat fragments, optionally inactivated and/or modified as defined in the present invention, and a polysulfated sugar such as dextran sulfate, pentosan polysulfate or heparin, in which the Tat oligomer is formed by noncovalent association by means of $Zn^{2+}$ ions. It is in particular an equimolar complex, for example with a heparin having a molecular weight of 15 000 Da or a heparin fragment having a molecular weight of 6000 Da.

According to yet another embodiment of said vaccine composition, it comprises a pharmaceutically acceptable vehicle and/or a carrier substance and/or an adjuvant.

According to an advantageous arrangement of this embodiment, said vaccine composition consists of a stabilized antigen as defined above and a pharmaceutically acceptable vehicle and/or a carrier substance.

The vaccine composition according to the invention is in a galenic form suitable for parenteral (subcutaneous, intramuscular, intravenous), enteral (oral, sublingual), or local (rectal, vaginal) administration.

The pharmaceutically acceptable vehicles, the carrier substances and the adjuvants are those conventionally used.

The adjuvants are advantageously chosen from the group consisting of: oily emulsions, mineral substances, bacterial extracts, saponin, alumina hydroxide, monophosphoryl-lipid A and squalene.

The carrier substances are advantageously selected from the group consisting of: unilamellar or multilamellar liposomes, ISCOMS, virosomes, virus-like particles, saponin micelles, solid microspheres which are saccharide (poly(lactide-co-glycolide)) or gold-bearing in nature, and nanoparticles.

According to another advantageous arrangement of this embodiment, said vaccine composition comprises alumina hydroxide.

According to yet another advantageous arrangement of this embodiment, said vaccine composition comprises at least one other HIV antigen, in particular Rev, Nef, gag or gp 160, or a fragment of at least 11 amino acids of said antigens.

A subject of the present invention is also a stabilized Tat antigen as defined above, as a vaccine for the prevention and/or treatment of an HIV infection in humans.

A subject of the present invention is also the use of a stabilized Tat antigen as defined above, for the preparation of a vaccine for use in the prevention and/or treatment of an HIV infection in humans.

A subject of the present invention is also a peptide complex, characterized in that it consists of:
  an HIV Tat protein or a Tat fragment of at least 11 amino acids, modified by substitution with a hydrophobic amino acid and/or the modification, with a hydrophobic group, of at least one amino acid of the Tat sequence, as defined above, associated with
  a metal ligand of Tat, and/or a non-metal ligand of Tat as defined above.

A subject of the present invention is also a protein or peptide fragment, characterized in that it is chosen from an HIV Tat protein or a Tat fragment of at least 11 amino acids, modified by substitution with a hydrophobic amino acid and/or the modification, with a hydrophobic group, of at least one amino acid of the Tat sequence, as defined above, with the exclusion of the substitutions R52L, R55L, R57L, R78A, G79A, E80A and K89L.

A subject of the present invention is also a method of preparing a stabilized Tat antigen, characterized in that it comprises at least:
  the preparation, by any appropriate means, of an HIV Tat protein or of a Tat fragment as defined above, and, simultaneously or sequentially,
  the formation of a complex with a Tat ligand as defined above and/or the substitution, with a hydrophobic amino acid, and/or the modification, with a hydrophobic group, of at least one of the amino acid residues of the Tat sequence, as defined above.

A subject of the present invention is also the use of a metal ion, preferably of a polyvalent cation, preferably of a divalent cation, such as $Zn^{2+}$ and Ce, for stabilizing the HIV Tat protein or a fragment of at least 11 amino acids to Tat; the use of a metal ion as defined above stabilizes Tat by protecting it against proteolytic degradation and by inhibiting the formation of covalent oligomeric forms.

A subject of the present invention is also a polynucleotide (DNA or RNA) or a mixture of polynucleotides selected from the group consisting of:

a) a polynucleotide or a mixture of polynucleotides comprising the sequence encoding an HIV Tat protein or a Tat fragment of at least 11 amino acids and the sequence encoding a peptide ligand of Tat, as defined above, and b) a polynucleotide comprising the sequence encoding an HIV Tat protein or a Tat fragment of at least 11 amino acids, modified by substitution, with a hydrophobic amino acid, of at least one amino acid of the Tat sequence, as defined above, with the exclusion of the substitutions R52L, R55L, R57L, R78A, G79A, E80A and K89L.

In accordance with the invention, the coding sequences of the Tat protein and/or the fragment of said protein and of the peptide ligand of Tat are included in a single polynucleotide or else in two separate polynucleotides.

A subject of the present invention is also a recombinant vector or a mixture of two recombinant vectors comprising an insert consisting, respectively, of the polynucleotide defined in a) or in b) and each of the two polynucleotides of the mixture defined in a).

Preferably, said recombinant vector is an expression vector in which said polynucleotide(s) is (are) placed under the control of appropriate regulatory elements for transcription and for translation.

A subject of the present invention is also prokaryotic or eukaryotic cells transformed with a recombinant vector or a mixture of recombinant vectors as defined above.

Numerous vectors into which it is possible to insert a polynucleotide of interest in order to introduce it into and to maintain it in a eukaryotic host cell are known per se; the choice of appropriate vector depends on the use envisaged for this sector (for example, replication of the sequence of interest, expression of this sequence, maintenance of the sequence in extrachromosomal form or else integration into the chromosomal material of the host), and also on the nature of the host cell. Use may be made, inter alia, of viral vectors such as adenoviruses, retroviruses, lentiviruses and AAVs, into which the sequence of interest has been inserted beforehand. It is also possible to insert the polynucleotide of interest into the sequence encoding a surface protein of the vector, at a site allowing exposure of the Tat antigen at the surface of the vector; it is in particular possible to insert the polynucleotide encoding Tat or a Tat fragment into the sequence of a viral capsid protein, so as to expose Tat at the surface of the particles of recombinant virus.

It is also possible to introduce said polynucleotides (isolated or inserted into a plasmid vector) into host cells, either by using physical methods such as electroporation or microinjection, or by associating them with any substance(s) making it possible to cross the plasma membrane, such as transporters, for instance nanotransporters, liposomes, lipids or cationic polymers. In addition, these methods can advantageously be combined, for example by using electroporation combined with liposomes.

The polynucleotides, the recombinant vectors and the transformed cells as defined above are useful in particular for the production of the stabilized Tat antigens according to the invention or as a vaccine for the prevention and/or treatment of an HIV infection in humans.

The polynucleotides according to the invention are obtained by conventional methods, known in themselves, according to standard protocols such as those described in *Current Protocols in Molecular Biology* (Frederick M. AUSUBEL, 2000, Wiley and Son Inc., Library of Congress, USA). For example, they can be obtained by PCR or RT-PCR amplification of a nucleic sequence, by screening of genomic DNA libraries for hybridization with a homologous probe, or else by complete or partial chemical synthesis. The recombinant vectors are constructed and introduced into host cells by conventional recombinant DNA and genetic engineering methods, which are known in themselves.

The Tat protein and its fragments, and also the derived peptide complexes and the modified proteins and peptides, as defined above, are prepared by conventional techniques known to those skilled in the art, in particular by solid-phase or liquid-phase synthesis or by expression of a recombinant DNA in an appropriate cell system (eukaryotic or prokaryotic).

More specifically:

the Tat protein and its fragments comprising amino acids modified with a hydrophobic group are synthesized by solid-phase, according to the Fmoc technique, originally described by Merrifield et al. (J. Am. Chem. Soc., 1964, 85: 2149-) (1964), and purified by reverse-phase high performance liquid chromatography, the Tat protein and its fragments comprising amino acids substituted with hydrophobic amino acids are produced from the corresponding cDNAs, obtained by any means of introducing mutations into a DNA sequence, known to those skilled in the art; the cDNA is cloned into a eukaryotic or prokaryotic expression vector and the protein or the fragment produced in the modified cells by the recombinant vector is purified by any appropriate means, in particular by affinity chromatography, and the peptide complexes are prepared by bringing Tat ligand(s) into contact with Tat or one of its fragments under conditions which allow the partners to interact.

The Tat antigens according to the invention have the following advantages compared with the antigens of the prior art:

due to their increased stability, they are more immunogenic; the anti-Tat antibody titers, in the animal, are at least 10 times higher than those obtained by immunization with nonmodified Tat or the Tat toxoid, the cysteines of which are blocked with acetamidomethyl groups, they induce both a humoral and cellular response; the comparative studies show that, under the same conditions, nonmodified Tat induces a weak humoral response but is not capable of inducing a cellular response, they have an impairment of their transactivating activity which indicates an absence of toxicity, they are homogeneous (preparation by reproducible methods) and well defined.

BRIEF DESCRIPTION OF THE DRAWINGS

Besides the above arrangements, the invention also comprises other arrangements which emerge from the description which follows, which refers to examples of use of the stabilized Tat antigen of the present invention, and also to the attached drawings in which.

EXAMPLE 1

Figure 1:
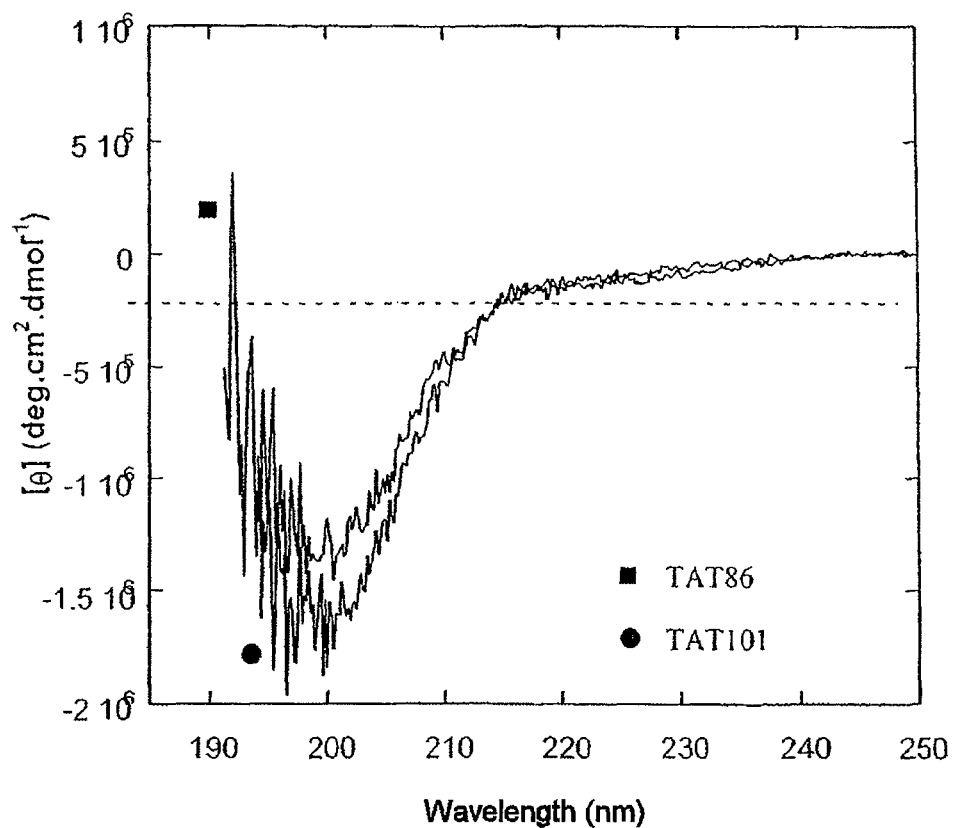
FIG. 1 illustrates the dichroic analysis of the structure of Tat86 (■) and Tat101 (●). Each spectrum is the result of four measurements in the distant UV region (190 nm-250 nm), obtained at a resolution of 0.2 nm, with an integration time of 0.5 sec and a bandwidth of 2 nm, on samples of Tat86 and Tat101 protein at the concentration of 15 µM in 5 mM potassium phosphate buffer, pH 7.0.

Preparation of Tat and of Derivatives Thereof

The Tat protein corresponds to that of the NDK isolate of HIV-1 (Groenink et al., J. Virol., 1991, 65, 1968-1975), the sequence of which is given in FIG. 2 (SEQ ID NO: 1). This protein is hereinafter referred to as Tat101. By analogy, the fragment 1 to 86 of this protein is hereinafter referred to as Tat86 (SEQ ID NO: 2). The NDK isolate of HIV-1 (SEQ ID NO: 1) represents the consensus sequence obtained from 66 sequences of primary HIV-1 isolates reported in the SWIS-SPROT and TrEMBL databases between 1999 and 2000.

1) Chemical Synthesis of Tat and of S-Tert-Butyl Derivatives Thereof (TatStBu)

The chemical synthesis of Tat is carried out in solid phase on an APPLIED BIOSYSTEMS 433A device, using the Fmoc/tert-butyl strategy known to those skilled in the art. The seven cysteine residues of the cysteine-rich region are protected with an S-tert-butyl (S(tBu)) group. Briefly, the synthesis scale is 1 mM, i.e. 500 mg of Fmoc-Asp(OtBu)-PAL-PEG-PS resin at 0.2 mmol/g for Tat101, and 476 mg of Fmoc-Glu(OtBu)-PAL-PEG-PS resin at 0.21 mmol/g for Tat86. 1 mM of each protected amino acid is used at each coupling cycle. The activation of each Fmoc amino acid is carried out using the dicyclohexylcarbodiimide/1-hydroxy-7-azabenzotriazole pair; the coupling is carried out in the presence of 0.25 M diisopropylethylamine/N-methylpyrrolidone. The cleavage of the resin and the deprotection (1 h and min) are carried out by mixing the dried resin (under vacuum overnight) with 10 ml of a solution of trifluoroacetic acid (TFA: 9.5)/triisopropylsilane (0.25)/water (0.25; V/V/V). After filtration on a sintered glass, the reaction mixture is precipitated in 100 ml of cooled (4° C.) tert-butyl methyl ether, and centrifuged for 15 minutes at 2500 rpm. The solid obtained is dissolved in 50 ml of a 15% aqueous solution of acetic acid, and then lyophilized. The synthesis crude obtained is purified by reverse-phase high performance liquid chromatography (HPLC), on a semi-preparative C4 column (21×250 mm, 5 µM, 300 Å JUPITER). The homogenized fraction for each derivative synthesized (Tat86C(22-37)StBu and Tat101C(22-37)StBu) is characterized, by virtue of its amino acid composition and by mass spectrometry.

A similar strategy was used to produce a Tat101 derivative in which cysteines 22, 34 and 37 are replaced with serines and cysteines 25, 27, 30 and 31 are protected with an S-tert-butyl group (Tat101C(22,34,37)S,C(25,27,30,31)StBu).

Tat86 and Tat101 are obtained from the above derivatives (Tat86C(22-37)StBu and Tat101C(22-37)StBu) by deprotection of the S-t-butyl groups. Briefly, 1 equivalent of protein and 50 equivalents of dithiothreitol per cysteine are dissolved in a degassed 50 mM sodium phosphate buffer, pH 8.5, containing 6M urea, for a final concentration of $10^{-4}$M. The progression of the reaction is monitored by reverse-phase high performance liquid chromatography (HPLC) on a C4 analytical column (15 cm×416 mm, 5 µM, 300 Å JUPITER). After 2 hours, the reaction appears to be quantitative, and the reaction mixture is acidified to pH 2 with an aqueous solution of TFA/$H_2O$ (50/50; V/V), and then diluted with an aqueous solution of TFA/$H_2O$ (1/999; V/V) in a final volume of 50 ml. The reaction mixture is then purified by reverse-phase high performance liquid chromatography (HPLC) on a semi-preparative C4 column (25 cm×10 mm, 5 µM, 300 Å JUPITER). The homogenized fraction for each derivative synthesized (Tat86 and Tat101) is characterized by virtue of its amino acids composition and by mass spectrometry.

A strategy similar to that used for Tat101 and Tat86 was used to synthesize:
- 18 overlapping peptides 15 amino acids in length, covering the sequence of Tat101,
- the Tat86 derivatives in which each of the seven cysteines of the cysteine-rich region is substituted to serine (Tat86Ser, control) or to a hydrophobic amino acid, such as leucine (Tat86C(22-37)L), a phenylalanine (Tat86C(22-37)F) or a tryptophan (Tat86C(22-37)W),
- the Tat101 derivative in which each of the arginines at positions 52 and 53 is substituted to glutamine (Tat101R(52,53)Q).

2) Production of Recombinant Tat Protein and of the Derived Mutants

The production of the recombinant Tat protein (Tat86 and Tat101) and of mutants thereof was carried out in *E. coli*. Briefly, the nucleotide sequence of the Tat protein was reconstituted using 8 overlapping synthetic nucleotide primers representing the sequence of the entire Tat gene encoding the abovementioned protein, flanked by the Nde I and Hind III restriction sites. The primers were hybridized by means of their complementary regions and the hybridization product obtained was then amplified by polymerase chain reaction (PCR) using the above primers, corresponding to the 5' and 3' ends of the Tat gene, flanked by the Nde I or Hind III restriction sites. The PCR amplification fragment was then cloned into the prokaryotic expression vector pET3a (NOVAGEN) and the Tat protein was expressed in *E. coli* from the recombinant vector thus obtained, according to the standard protocols recommended by the supplier. The recombinant Tat protein was purified by passage over a heparin column and then by reverse-phase high pressure chromatography, according to standard chromatography protocols.

Alternatively, the Tat gene was cloned into the plasmid pTriEx-1 (NOVAGEN), which allows the expression of Tat in *E. coli*, or in insect cells or mammalian cells under the control, respectively, of the T7 promoter, of the p10 promoter, and of a promoter which is a hybrid between the activator of the cytomegalovirus early promoter and the chicken β-actin promoter.

A similar strategy was used to produce Tat86 mutants in which each of the seven cysteines of the cysteine-rich region is substituted to serine (Tat86Ser, control) or to a hydrophobic amino acid, such as a leucine (Tat86C(22-37)).

3) Preparation of Tat Complexed with Polysulfated Sugars or with Metal Ions ($Zn^{2+}$)

Heparin (molecular weight 15 000; H3393 (SIGMA)) and its fragments of molecular weight 6000 (H5284, SIGMA) and 3000 (H3400, SIGMA) were mixed with Tat101 or Tat86 in PBS buffer, in a Tat/heparin molar ratio of 1/1, and the complexes were incubated at 20° C. for a period of time between 1 hour and overnight. The complexes obtained from Tat101 are called Tat101/Hep3000, Tat101/Hep6000 and Tat101/Hep15 000, and similarly for Tat86. Complexes between Tat101 or Tat86 and other polysulfated sugars such as dextran sulfate (Dextran; D7037, SIGMA) and pentosan polysulfate (PPS; SIGMA) were prepared as indicated above for the complexes between Tat and heparin. The complexes thus obtained from Tat101 are called Tat101/Dextran and Tat101/PPS.

A similar strategy was used to prepare complexes between Tat101 or Tat86 and $Zn^{2+}$ ions (Tat101/Zn; Tat86/Zn).

Complexes between Tat101, Tat86 or inactivated derivatives of Tat, such as Tat101R(52,53)Q, and two ligands other than Tat, such as polyvalent cations, in particular divalent cations such as $Zn^{2+}$, and a polysulfated sugar such as heparin, were also prepared. More specifically, the two ligands are mixed with Tat, in PBS buffer (Tat/heparin equimolar ratio; $ZnCl_2$ in a 6-fold excess, relative to Tat), and the mixture is then incubated for one hour at ambient temperature. The complexes thus obtained are called Tat101/Zn/Hep6000 and Tat101R(52,53)Q/Zn/Hep6000.

4) Preparation of Tat Oligomers

Covalent dimers of Tat were prepared by oxidation of the cysteine residues. More specifically, a monomeric derivative of Tat, such as, for example, the derivative Tat101C(22-31; 37)S, was dissolved in 50 mM sodium phosphate buffer, pH 8 (final concentration $10^{-4}$M). The solution was incubated for 48 hours at ambient temperature (approximately 20° C.), with stirring. The reaction medium was then acidified to pH 2 with a solution containing TFA (TFA/$H_2O$, 1/1, v/v). The Tat dimer was finally purified by reverse-phase high performance liquid chromatography using an analytical C4 column (15 cm×4.6 mm, 5 µM, 300 Å JUPITER). The dimeric nature of the Tat derivative was verified by amino acid analysis and mass spectrometry.

EXAMPLE 2

Tat is Structurally Flexible and Particularly Sensitive to Proteolytic Degradation 1) Materials and Methods
a) Preparation of Tat Tat86 and Tat101 are produced by chemical synthesis or by recombinant DNA techniques, as described in Example 1.

b) Analysis of the Susceptibility of Tat101 to Proteolysis

The Tat101 protein was dissolved extemporaneously in 50 mM potassium phosphate buffer, pH 7.0, at the final concentration of 0.1 g/l, and then incubated at 37° C. with the enzyme (trypsin or chymotrypsin, Roche Diagnostics GmbH) in an enzyme/substrate ratio of 1/200 (W/W). At various incubation times (30 sec, 1 min, 2 min, 5 min, 6 min), 5 µl of 5% TFA were added in order to stop the enzymatic digestion, and the peptide fragments produced were identified by liquid chromatography coupled on line to mass spectrometry (ESI-MS, Quattro II, Micromass).

c) Dichroic Analysis of the Tat86 and Tat101 Proteins

The circular dichroism measurements were carried out using a dichrograph (CD6, Yvon Jobin), at ambient temperature. The solutions of samples at 15 µM in 5 mM potassium phosphate buffer, pH 7.0, were filtered beforehand through 0.45 µm membranes, before being transferred into quartz cuvettes with a 2 mm optical path length. Each spectrum is the result of four measurements in the far-UV region (190 nm-250 nm), obtained at a resolution of 0.2 nm, with an integration time of 0.5 sec and a bandwidth of 2 nm.

2) Results

Figure 2:
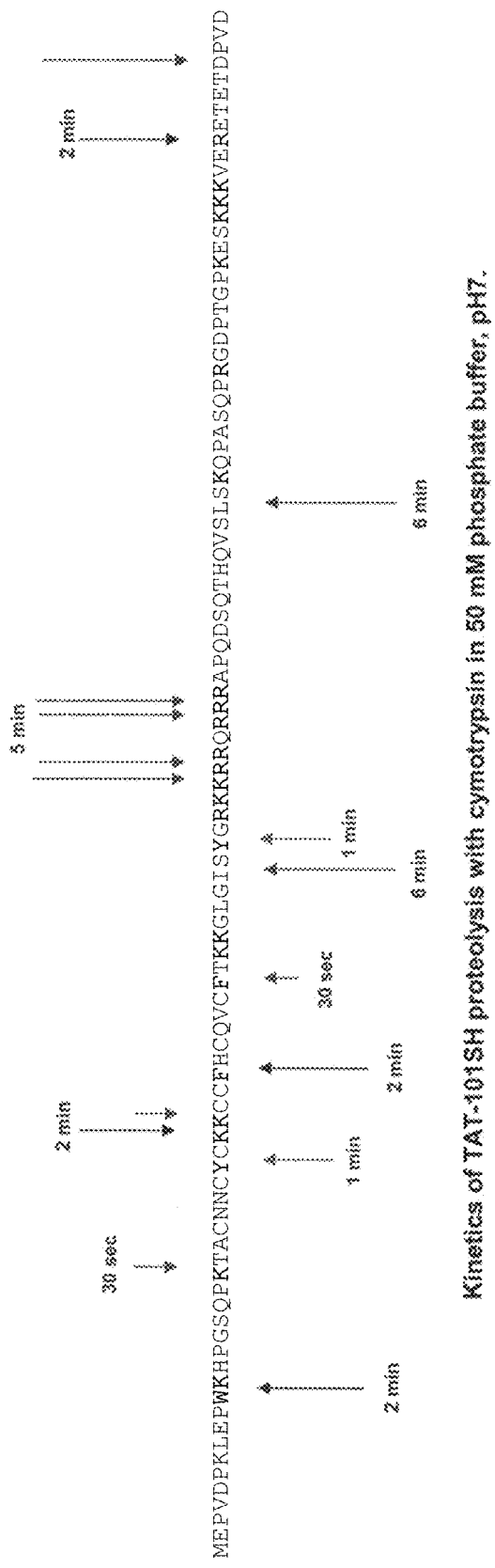
FIG. 2 illustrates the kinetics of proteolysis of TAT101; free Tat101 protein (TAT-101SH; 10 µg/100 µl) was incubated at 37° C. in the presence of trypsin (upper panel) or of chymotrypsin (lower panel), in 50 mM potassium phosphate buffer, pH 7 (enzyme/substrate ration 1/200 (W/W)). The Tat101 protein sequence of SEQ ID NO: 1 is shown for reference. The peptide fragments generated at various digestion times (30 sec, 1 min, 2 min, 5 min and 6 min) are materialized by means of arrows indicating the trypsin cleavage sites (basic amino acids: arginine (R) or lysine (K)) or chymotrypsin cleavage sites (aromatic amino acids: tyrosine (Y), phenylalanine (F) or tryptophan (W) then hydrophobic aliphatic amino acids: leucine (L) or isoleucine (I), in decreasing preferential order)

The circular dichroism studies show that the Tat86 and Tat101 proteins both lack a secondary structure (FIG. 1) and indicate that they adopt a flexible structure, devoid of β-sheets and α-helices. Weak structural organization of a protein induces considerable flexibility and, consequently, a low thermodynamic stability and a high susceptibility to proteolysis. This is the case of the Tat protein, since it is particularly sensitive to proteolytic degradation. Specifically, the analysis carried out with the 101 amino acid Tat protein shows that it undergoes a first cleavage after only 30 seconds of incubation at 37° C. with trypsin or chymotrypsin (FIG. 2).

The inventors put forward the hypothesis that improving the stability of Tat should decrease its proteolytic susceptibility and increase its half-life in the organism, and also its immunogenicity. This hypothesis was validated by comparing the immunogenicity of unmodified Tat with that of prestabilized Tat molecules. The stabilization of Tat was undertaken either by complexation with a ligand, or by incorporation of hydrophobic groups.

EXAMPLE 3

Stabilization of Tat by Formation of Complexes Between Tat101 and a Tat Ligand (Heparin, $Zn^{2+}$)

1) Materials and Methods
a) Production of Tat/Ligand Complexes

The Tat86 and Tat101 proteins, free or complexed with heparin or alternatively with $Zn^{2+}$ ion, are produced as described in Example 1.

b) Analysis of the Susceptibility of Tat101 and of Tat101/Heparin to Proteolytic Degradation The analysis is carried out under the conditions described in Example 2, with the exception of the incubation period with trypsin, which is 15 min, and of the concentration of Tat protein, which is 0.5 g/l.

c) Analysis of the Antibody Response Induced by Tat

The analysis of the antibody response induced by Tat and its derivatives was carried out in the BALE/c mouse and the SWISS mouse (outbred). The various immunogens were mixed at equal volume with alumina hydroxide and then injected, intraperitoneally, at a rate of 5 µg of Tat protein per BALB/c mouse, in a final volume of 100 µl. The mice were immunized twice, 14 days apart. A blood sample was taken 14 and 28 days after the second immunization.

Alternatively, SWISS mice were immunized with Tat and its derivatives, in the absence of adjuvant, subcutaneously, at a rate of 16 µg of Tat protein per mouse, in a final volume of 100 µl. The mice were immunized twice, 14 days apart. A blood sample was taken 14 days after the second immunization.

The sera were then tested for the presence of anti-Tat antibodies by means of an immunoenzymatic assay (ELISA). In these experiments, Tat was preadsorbed onto ELISA plates. The ELISA plates were saturated with 0.1% bovine serum albumin. Serum dilutions were finally incubated on the plates overnight at 4° C. The presence of anti-Tat antibodies was visualized using a peroxydase-coupled goat antibody specific for mouse antibodies, and ABTS as a substrate.

d) Antigenic Profile of the Sera Produced by Immunization with Tat101 and Tat101/Hep6000

This profile was established using an immunoenzymatic assay. 18 overlapping peptides 15 amino acids in length, representing the entire Tat sequence, were synthesized in solid phase, as described in Example 1. The peptides were then adsorbed onto ELISA plate wells (10 µg/100 µl/well). The ELISA plates were saturated with 0.1% bovine serum albumin. Dilutions of the anti-Tat101 and Tat101/heparin6000 serum samples to be tested were then added to the plates and the incubation was continued overnight at 4° C. The presence of anti-Tat antibodies was then visualized using a peroxydase-coupled goat antibody specific for mouse antibodies, and ABTS as substrate.

Figure 3:
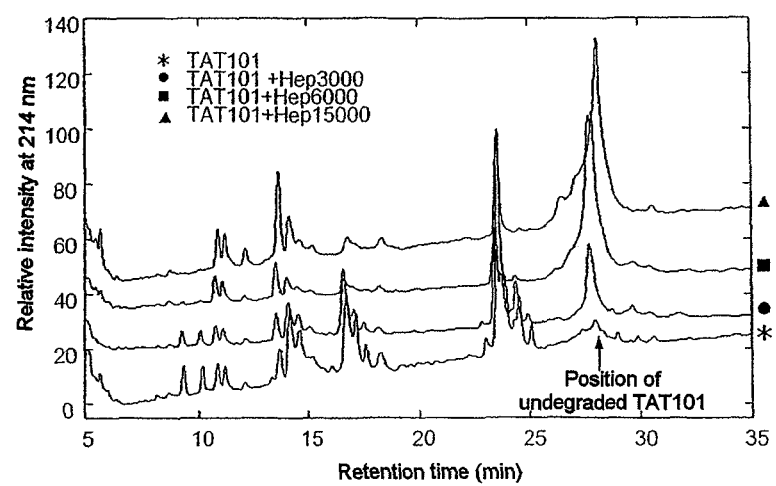
FIG. 3 illustrates the comparative analysis by reverse-phase high performance liquid chromatography of the profile of the peptides generated by enzymatic digestion of TAT101 (10 µg/100 µl) and of each of the TAT101/heparin equimolar complexes (corresponding to 10 µg of TAT101 in 100 µl). The Tat101 protein (*) and the Tat101/Hep 3000 (●), Tat101/Hep 6000 (■) and Tat101/Hep 15 000 (□) complexes were incubated for 15 min at 37° C. in the presence of trypsin, in 50 mM potassium phosphate buffer, pH 7 (enzyme/substrate ratio 1/200 (W/W)). The arrow indicates the position of nondegraded Tat101.
Figure 4:
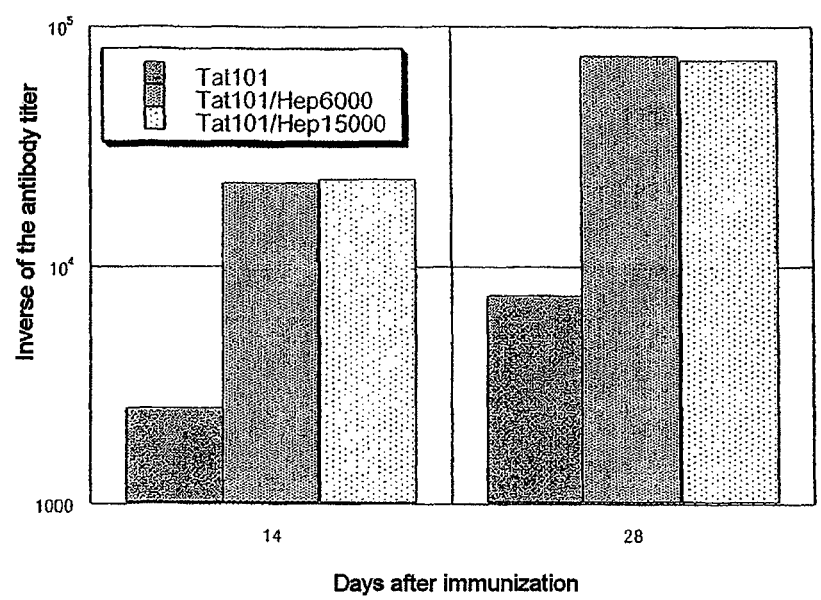
FIG. 4 illustrates the comparative analysis, by ELISA, of the immunogenicity of Tat101, Tat101/Hep15 000 and Tat101/Hep6000 in BALB/c mice. The values indicated correspond to the inverse of the antibody titer, measured 14 days and 28 days after the last immunization.

2) Results a) The Formation of Complexes Between Tat and a Ligand to Tat101 Makes it Possible to Increase the Stability of Tat101 with Respect to Proteolysis Three types of Tat/heparin complexes with a Tat/ligand molar ratio of 1/1 were prepared from Tat101 and heparins of molecular mass 15 000, 6000 and 3000, which exhibit a decreasing affinity for the protein. The comparative analysis of the susceptibility to proteolysis of the free Tat protein and of the complexed Tat protein shows that free Tat is completely degraded in 15 minutes whereas it is degraded more slowly when it is complexed (FIG. 3). The low-affinity heparin 3000 fragment gives relatively little protection of Tat, whereas the heparin 15 000 and the heparin 6000 fragment, which have a high affinity, give better protection of the protein (FIG. 3). Thus, the formation of complexes between Tat and heparin or heparin fragments makes it possible to stabilize Tat with respect to proteolytic degradation. To a lesser degree, the formation of complexes between Tat and $Zn^{2+}$ also makes it possible to stabilize Tat with respect to proteolytic degradation (Table I: see Example 6, results).

b) The Formation of Complexes Between Tat and Heparin Makes it Possible to Increase the Humoral Response Induced Against Tat The anti-Tat antibody response induced by immunization of BalB/c mice with either Tat101 mixed with alumina hydroxide, or Tat101/Hep15 000 or Tat101/Hep6000 complexes mixed with alumina hydroxide, was analyzed by ELISA. The results show that the humoral response is increased when Tat101 is complexed beforehand with heparin 15 000 or 6000 (FIG. 4); the antibody titers induced by Tat101 are ten times lower than those induced by Tat101/Hep15 000 and Tat101/Hep6000.

Figure 13:
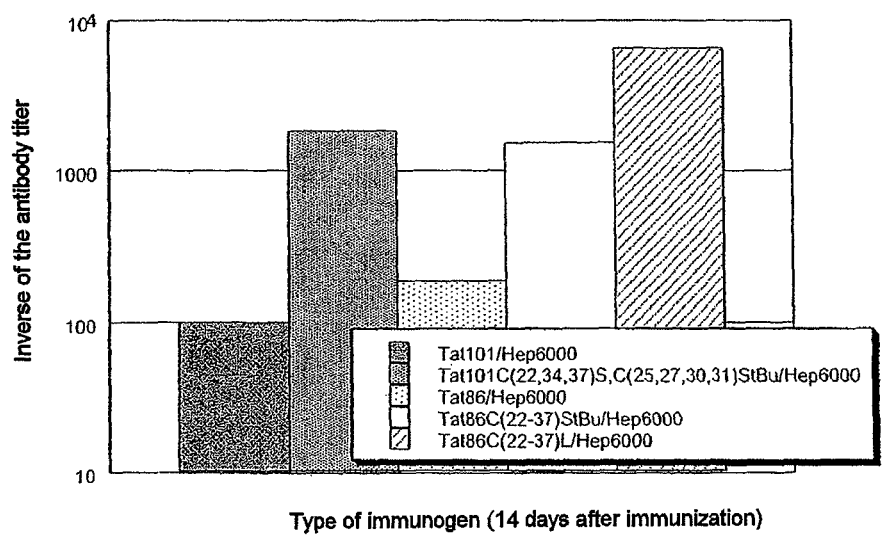
FIG. 13 illustrates the analysis by ELISA of the immunogenicity of Tat101/Hep6000, Tat101C(22,34,37)S, C(25,27,30,31)StBu/Hep6000, Tat86/Hep6000, Tat86C(22-37)StBu/Hep6000 and Tat86C(22-37)L/Hep6000, in the absence of adjuvant, in SWISS (outbred) mice. The values indicated correspond to the inverse of the antibody titer, measured 14 days after the last immunination.

Similar experiments, carried out in SWISS mice and in the absence of adjuvant, show that the Tat/heparin complexes (Tat101/Hep6000 and Tat86/Hep6000) are also capable of inducing an immune response in an outbred population, in the absence of adjuvant (FIG. 13).

In addition, since the interaction with the heparin ligand could mask certain antigenic sites of Tat and unmask others thereof, and induce a humoral response against determinants which are not those naturally presented by the free Tat protein, the antigenic specificity of the antibodies produced against Tat101 and Tat101/Hep6000 was analyzed by ELISA. To do this, the sera of the mice immunized with Tat101 and Tat101/Hep6000 were incubated in the presence of a series of 18 overlapping peptides 15 amino acids in length, representing the entire Tat sequence.

Figure 5:
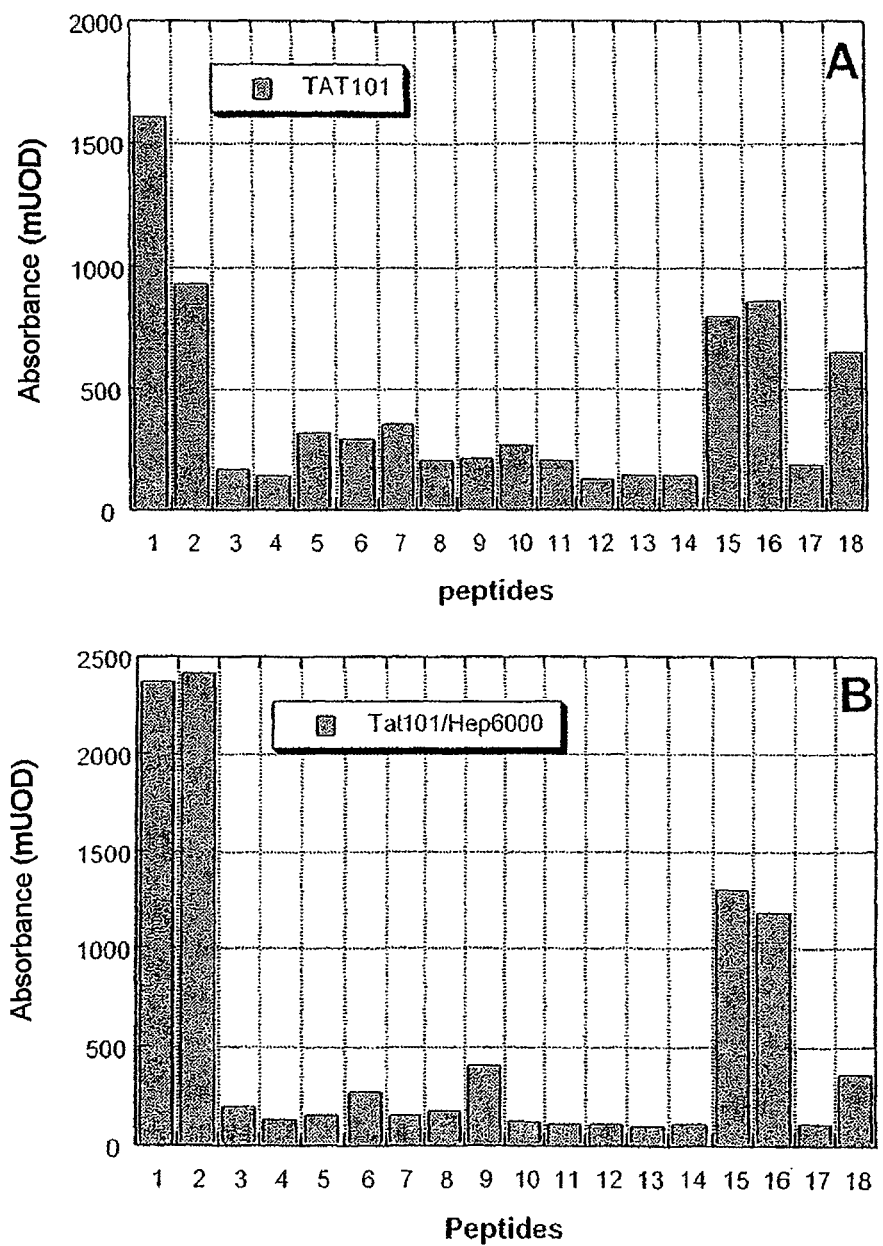
FIG. 5 represents the antigenic profile of the sera produced by immunization of BALB/c mice with Tat101 (A) and Tat101/Hep6000 (B). The sera are assayed by ELISA with respect to 18 overlapping peptides 15 amino acids in length, representing the entire Tat sequence (peptides 1 to 18). The absorbance values are expressed as milliunits of optical density (mUOD)

The results given in FIG. 5 show that the antigenic specificity of the anti-Tat antibodies produced by immunization with Tat101/Hep6000 is similar to that produced by immunization with free Tat101.

Specifically, immunization with Tat101 induces predominantly antibodies directed against region 1-15 (titer >1/3000), and more weakly antibodies against regions 71-90 and 86-101 (titer <1/400). The sera derived from the immunization with Tat101/heparin exhibit the same antigenic profile. Furthermore, in both cases, the immunodominant region is located in the N-terminal region. The complexation of Tat with heparin 6000 makes it possible to increase the strength of the humoral response without modifying the antigenic specificity of the anti-Tat antibodies produced.

EXAMPLE 4

Stabilization of Tat by Incorporation of Hydrophobic Groups

1) Materials and Methods
a) Production of Tat and of Derivatives Thereof.

Tat and derivatives thereof in which the cysteine residues are blocked using hydrophobic groups of the S-tert-butyl (StBu) type are synthesized in solid phase, as described in Example 1.

b) Analysis of the Susceptibility of Tat86 and Tat86C(22-37)StBu to Proteolytic Degradation The Tat86 and Tat86C(22-37)StBu proteins were dissolved extemporaneously in 50 mM potassium phosphate buffer, pH 7.0, at a final concentration of 0.5 g/l of Tat protein, and then incubated at 37° C. with pronase E (Roche Diagnostics GmBH), in an enzyme/substrate ratio of 1/20 (W/W). After incubation for 15 min, 5 µl of 5% TFA were added in order to stop the enzymatic digestion, and the peptide fragments produced were identified by liquid chromatography coupled on line to mass spectrometry (ESI-MS, Quattro II, Micromass).

c) Analysis of the Antibody Response Induced by Tat86 and Tat86C(22-37)StBu, in the Animal This analysis was carried out as described in Example 3 for the Tat/heparin complexes, with the exception that the sera were taken either 14 and 28 days (FIG. 9), or 25, 35 and 47 days (FIG. 8), after the final immunization.

d) Analysis of the Cellular Response Induced by Tat and Derivatives Thereof.

The various immunogens were prepared and injected according to the same protocol as that described for the induction of the humoral response (Example 3). Ten days after the second immunization, the spleens of the animals were removed and cut into pieces. The mouse splenocytes were then incubated in the presence of series of dilution of Tat86. After stimulation for 3 days at 37° C., triturated thymydine was added, and 18 hours later, the cells were removed and the cell proliferation was evaluated by measuring the radioactivity to be incorporated, according to standard protocols.

e) Analysis of the Heparin-Binding of Tat and of its Hydrophobic Derivatives

The Tat86, Tat86C(22-37)L and Tat86C(22-37)StBu antigens were adsorbed in the wells of an ELISA plate (0.1 µg/well). The plates were then saturated with 0.1 M phosphate buffer, pH 7, containing 0.3% bovine serum albumin. Series of dilutions of a heparin-albuminbiotin conjugate were then added to the wells. After incubation overnight at 4° C., the amount of the heparinalbumin-biotin conjugate bound to Tat86 or to its derivatives was visualized using peroxydase-coupled streptavidin and then ABTS as substrate.

Figure 6:
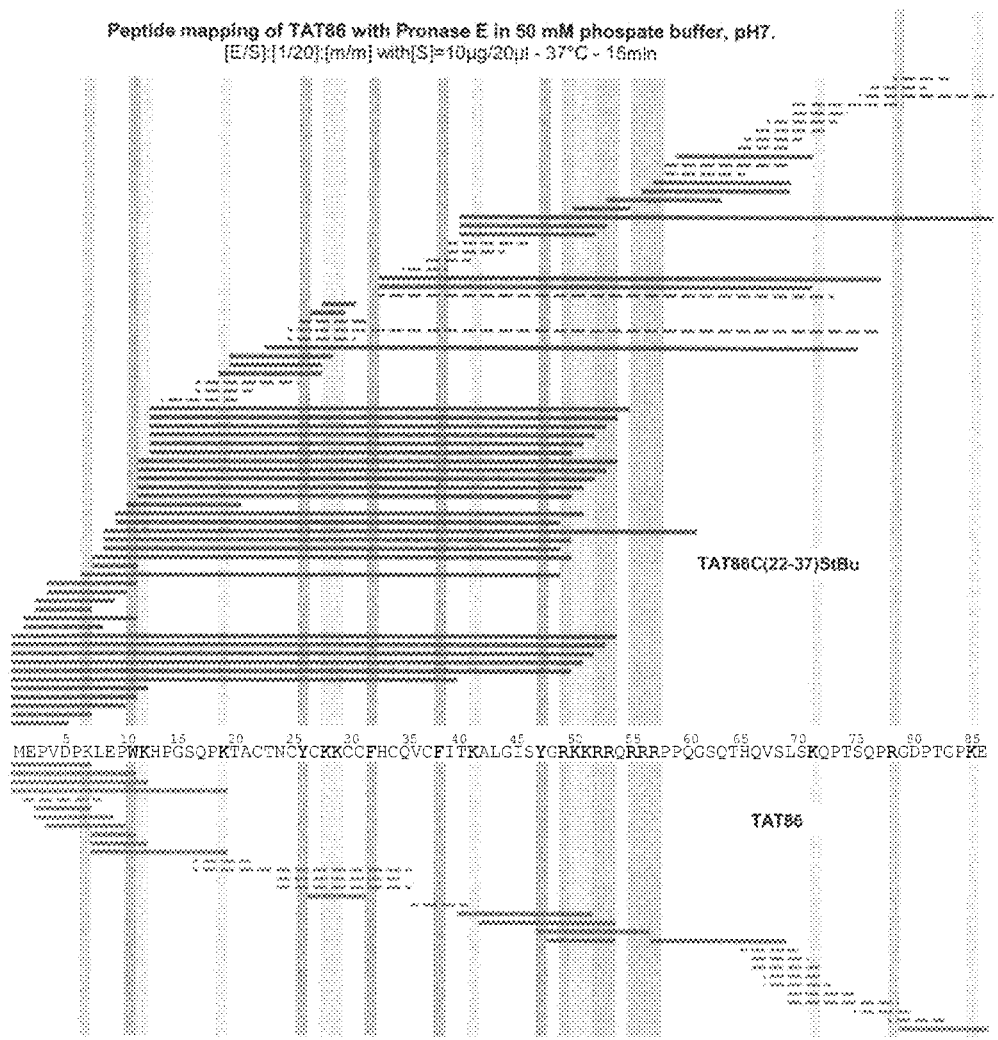
FIG. 6 represents the peptide mapping of the fragments generated by digestion with pronase E, of free Tat86 (TAT86: lower panel) or Tat86 modified with S-tert-butyl groups (TAT86 C(22-37)StBu: upper panel). The Tat86 protein sequence of SEQ ID NO: 3 is shown for reference. The digestion is carried out for 15 min at 37° C. in 50 mM potassium phosphate buffer, pH 7, with an enzyme/substrate ratio of 1/20 (W/W) and a Tat substrate at the final concentration of 10 µg/20 µl.
Figure 7:
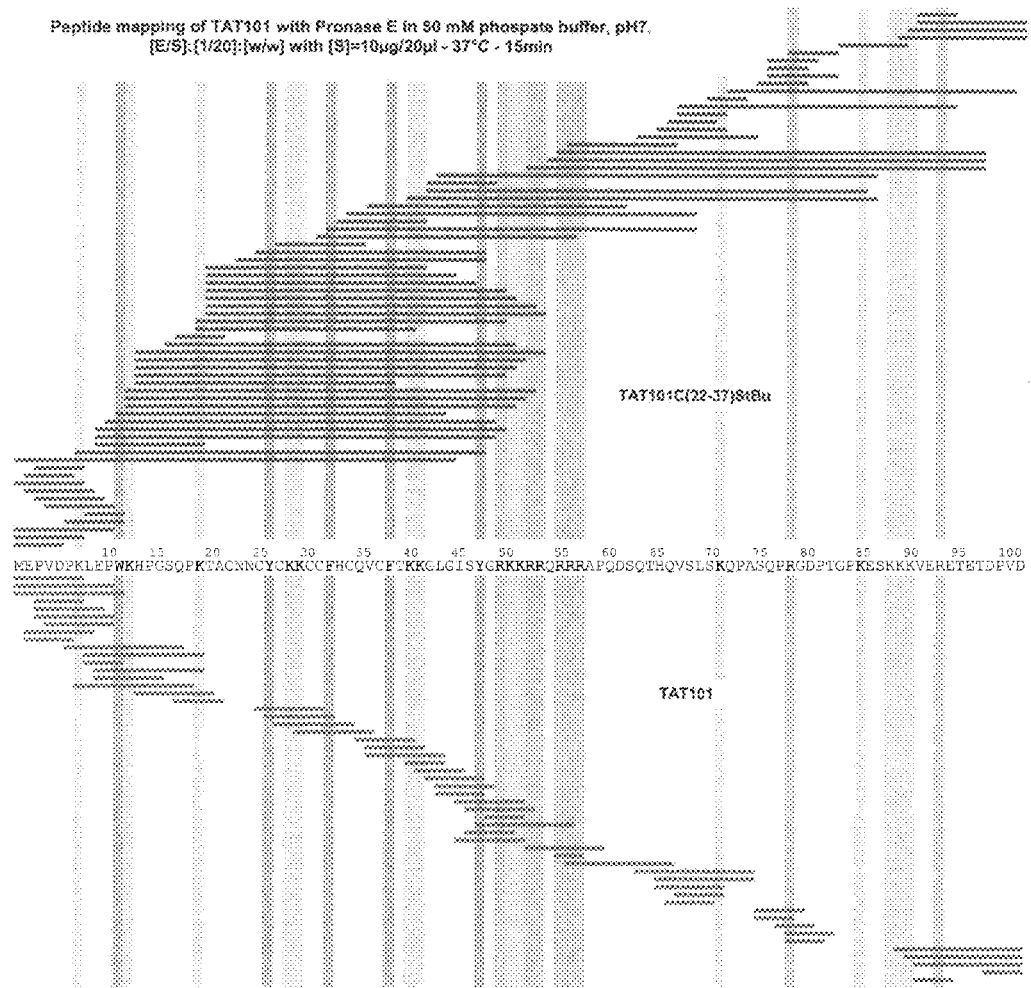
FIG. 7 represents the peptide mapping of the fragments generated by digestion with pronase E, of free Tat101 (TAT101: lower panel) or Tat101 modified with S-tert-butyl groups (TAT101 C(22-37)StBu: upper panel). The Tat101 protein sequence of SEQ ID NO: 1 is shown for reference. The digestion is carried out for 15 min at 37° C. in 50 mM potassium phosphate buffer, pH 7, with an enzyme/substrate ratio of 1/20 (W/W) and a Tat substrate at the final concentration of 10 µg/20 µl.
Figure 8:
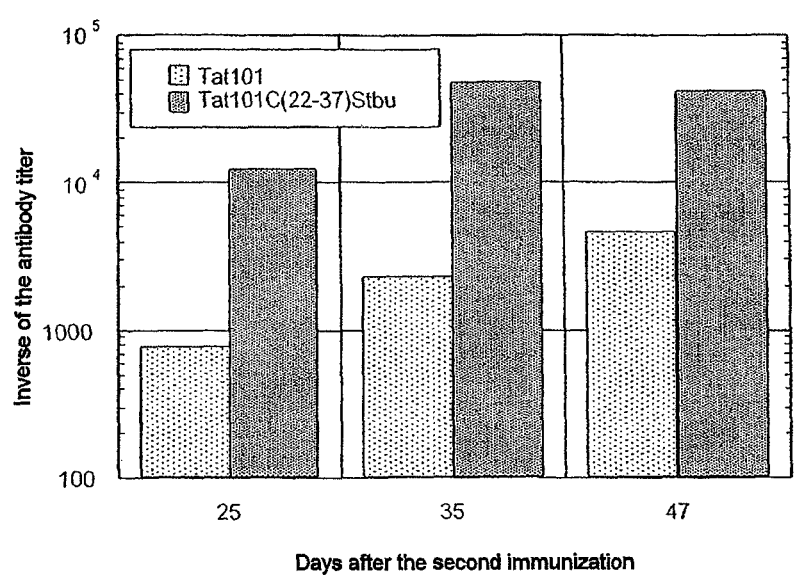
FIG. 8 illustrates the comparative analysis by ELISA of the immunogenicity of Tat101 and Tat101C(22-37)StBu in BALB/c mice. The values indicated correspond to the inverse of the antibody titer, measured 25 days, 35 days and 47 days after the last immunization.
Figure 9:
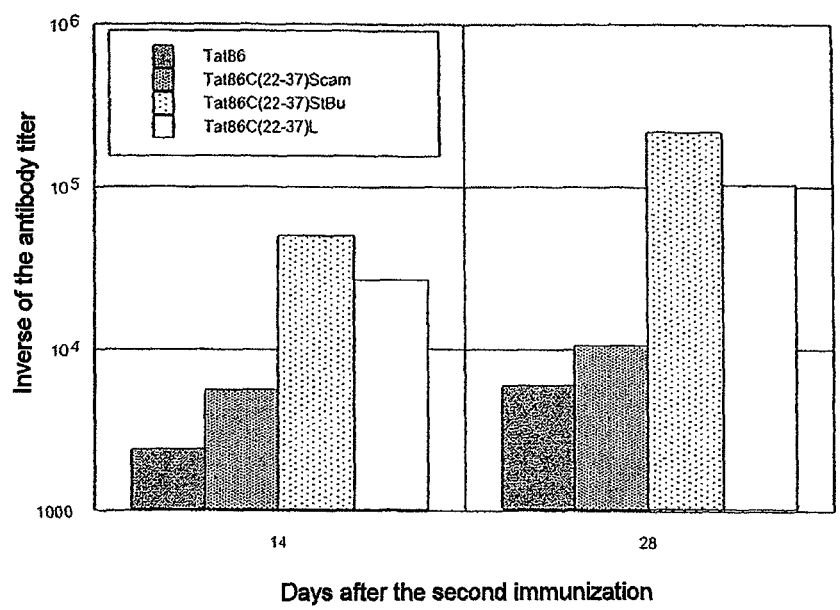
FIG. 9 illustrates the comparative analysis by ELISA of the immunogenicity of Tat86, Tat86C(22-37)StBu, Tat86C(22-37)L and of a Tat toxoid prepared by carboxamidation (Tat86C(22-37)Scam) in BALB/c mice. The values indicated correspond to the inverse of the antibody titer, measured 14 days and 28 days after the last immunization.

2) Results
a) Blocking of the Tat Cysteines with StBu Groups Makes it Possible to Increase the Stability of a Large Part of the Tat Sequence In the second approach, the Tat protein was stabilized by incorporation of hydrophobic groups, with the aim of creating a stabilizing core. The 7 cysteines located between the residue at position 22 and the residue at position 37 of the cysteine-rich region of Tat were modified using hydrophobic groups of the S-tert-butyl (StBu) type. In order to evaluate the effects of this type of modification on the stability of Tat, a Tat86 protein, the 7 cysteines of which are blocked with StBu groups (Tat86C(22-37)StBu), and another in which the cysteines are free (Tat86), were synthesized. Similarly, a Tat101 protein with the cysteines free (Tat101) and a Tat101 protein with the cysteines blocked with StBus (Tat101C(22-37)StBu) were also synthesized. The comparative analysis of the stability of these four proteins with respect to the proteolytic action of pronase shows considerable differences between the fragments derived from the proteolysis of each of the four proteins (FIGS. 6 and 7). Thus, the fragments derived from Tat101 and Tat86 are mostly small in size, whereas those derived from Tat101C(22-37)StBu and Tat86C(22-37)StBu are predominantly large in size. These results indicate that the Tat proteins in which the cysteines are free are extensively proteolyzed, whereas those in which the cysteines are blocked with hydrophobic groups are partially protected against the enzymatic action. The presence, in the product of digestion of Tat101C(22-37)StBu and Tat86C(22-37)StBu, of numerous long fragments in the region extending from amino acid 13 to amino acid 52 and of several long fragments in the C-terminal region indicates that the protection with respect to the enzymatic action is exerted in the hydrophobic group insertion region but also at a distance therefrom.

b) The Blocking of the Tat Cysteines with Hydrophobic Groups of the StBu Type Makes it Possible to Increase the Humoral Response Directed Against Tat Firstly, the effect of the incorporation of StBu groups on the immunogenicity of the long form of Tat (Tat101) was evaluated. The results show that Tat101 induces an antibody response which is 15 times weaker than that induced by Tat101C(22-37)StBu (FIG. 8). The comparative analysis of the immunogenicity of the short form of Tat (Tat86), of Tat86C(22-37)StBu and of a Tat toxoid prepared by carboxamidation (Tatcam) shows that Tat86C(22-37)StBu induces an antibody response which is more than 30 times greater than that provided by Tat86 and ten times greater than that induced by the Tatcam toxoid (FIG. 9). Thus, the incorporation of StBu groups makes it possible to significantly increase the immunogenicity of Tat101 and of Tat86.

Figure 10:
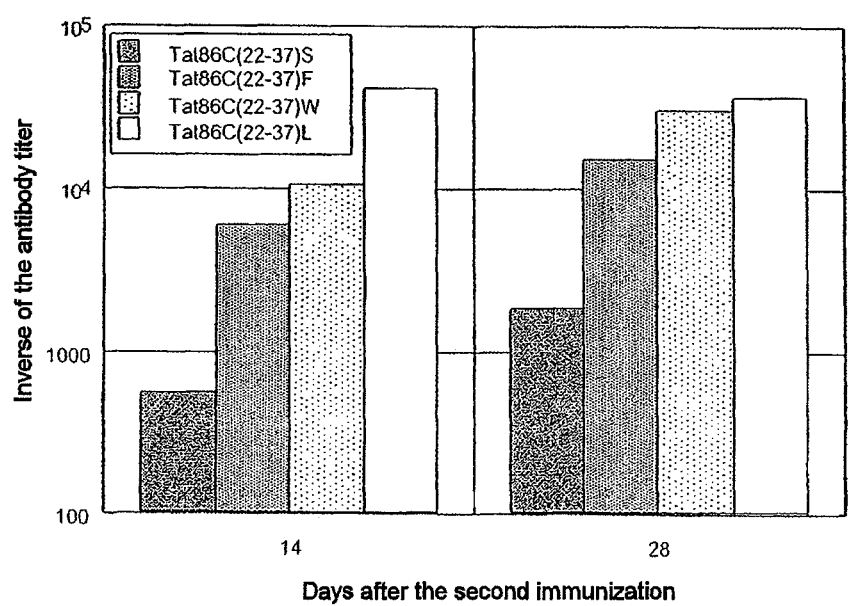
FIG. 10 illustrates the comparative analysis by ELISA of the immunogenicity of the Tat86C(22-37)S, Tat86C(22-37)F, Tat86C(22-37)W and Tat86C(22-37)L derivatives in BALE/c mice. The values indicated correspond to the inverse of the antibody titer, measured 14 days and 28 days after the last immunization.

Similar experiments, carried out in SWISS mice and in the absence of adjuvant, show that the TatStBu derivatives are also capable of inducing an immune response in an outbred population, in the absence of adjuvant (FIG. 13).

c) The Hydrophobic Groups Incorporated into Tat are Responsible for the Increase in Immunogenicity The role of hydrophobic groups in the increase in the immunogenicity of Tat was demonstrated by studying the immunogenicity of a Tat86 molecule in which the 7 cysteines are substituted, respectively, with leucines (Tat86C(22-37)L), phenylalanines (Tat86C(22-37)F) or tryptophans (Tat86C(22-37)W), by comparison with a Tat molecule in which the 7 cysteines are replaced with serines (Tat86C(22-37)S) (FIG. 10).

d) The Combination of the Complexation with Heparin and the Creation of a Hydrophobic Zone Increases the Immunogenicity of Tat The results given in Examples 3 and 4 demonstrate that it is possible to substantially increase the immunogenicity of Tat, either by creation of a hydrophobic zone in the molecule, or by formation of complexes. These two approaches were set out using two distinct regions of Tat. Specifically, the formation of complexes with heparin is mediated by the basic region of Tat, located from residue 49 to residue 57, whereas the 7 cysteines are grouped together in zone 22-37 of the molecule.

Consequently, studies were carried out in order to verify, firstly, that the Tat molecules of hydrophobic nature could still interact with heparin, and then to demonstrate whether the newly formed compounds exhibited further increased immunogenic characteristics.

Figure 11:
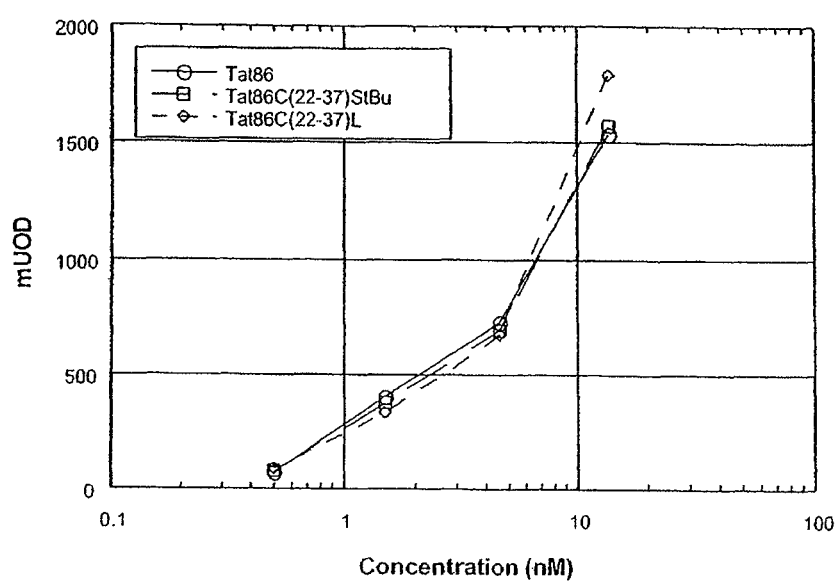
FIG. 11 illustrates the comparative analysis by ELISA of the binding of Tat86, Tat86C(22-37)StBu and Tat86C(22-37)L to heparin 6000. The absorbance values are expressed in milliunits of optical density (mUOD)

The study of the heparin-binding of Tat86, Tat86C(22-37) StBu and Tat86C(22-37)L using an ELISA assay shows that the three molecules exhibit the same ability to bind heparin (FIG. 11).

After immunization of BALB/c mice with free Tat86C(22-37)StBu complexed beforehand with heparin 6000, under conditions as described in Example 3 for the Tat derivatives, the antibody response was analyzed by ELISA.

Figure 12:
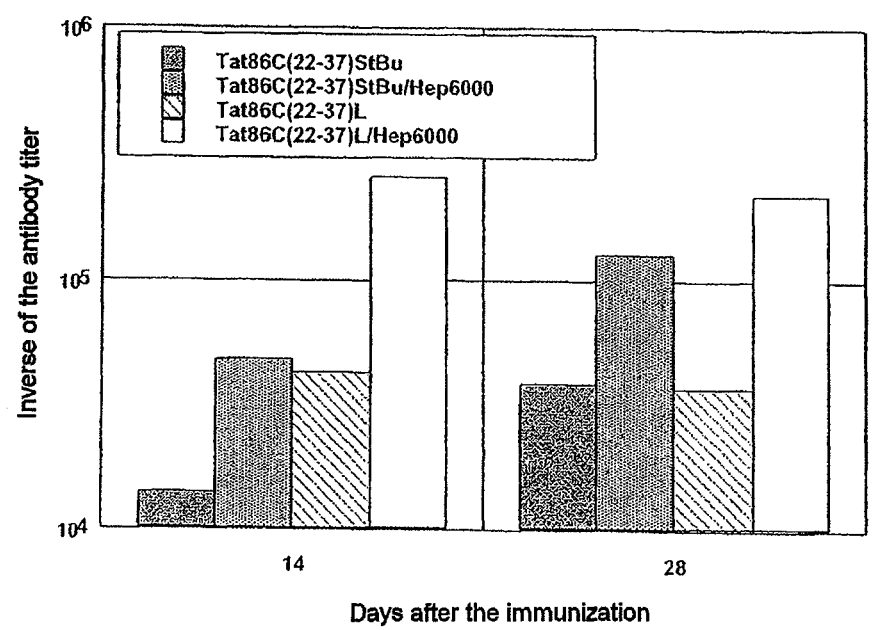
FIG. 12 illustrates the comparative analysis by ELISA of the immunogenicity of Tat86C(22-37)StBu and Tat86C(22-37)L, in free form or in heparin-complexed form. The values indicated correspond to the inverse of the antibody titer, measured 14 days and 28 days after the last immunization.

The antibody titers obtained by immunization with the Tat86C(22-37)StBu/Hep6000 complex are five times greater than those induced by immunization with Tat86C(22-37) StBu (FIG. 12). These results indicate that the complexation with heparin also increases the immunogenicity of the Tat derivatives and that the combination of the two modifications thus makes it possible to obtain an increase in immunogenicity greater than that obtained with each of the modifications alone.

Figure 14:
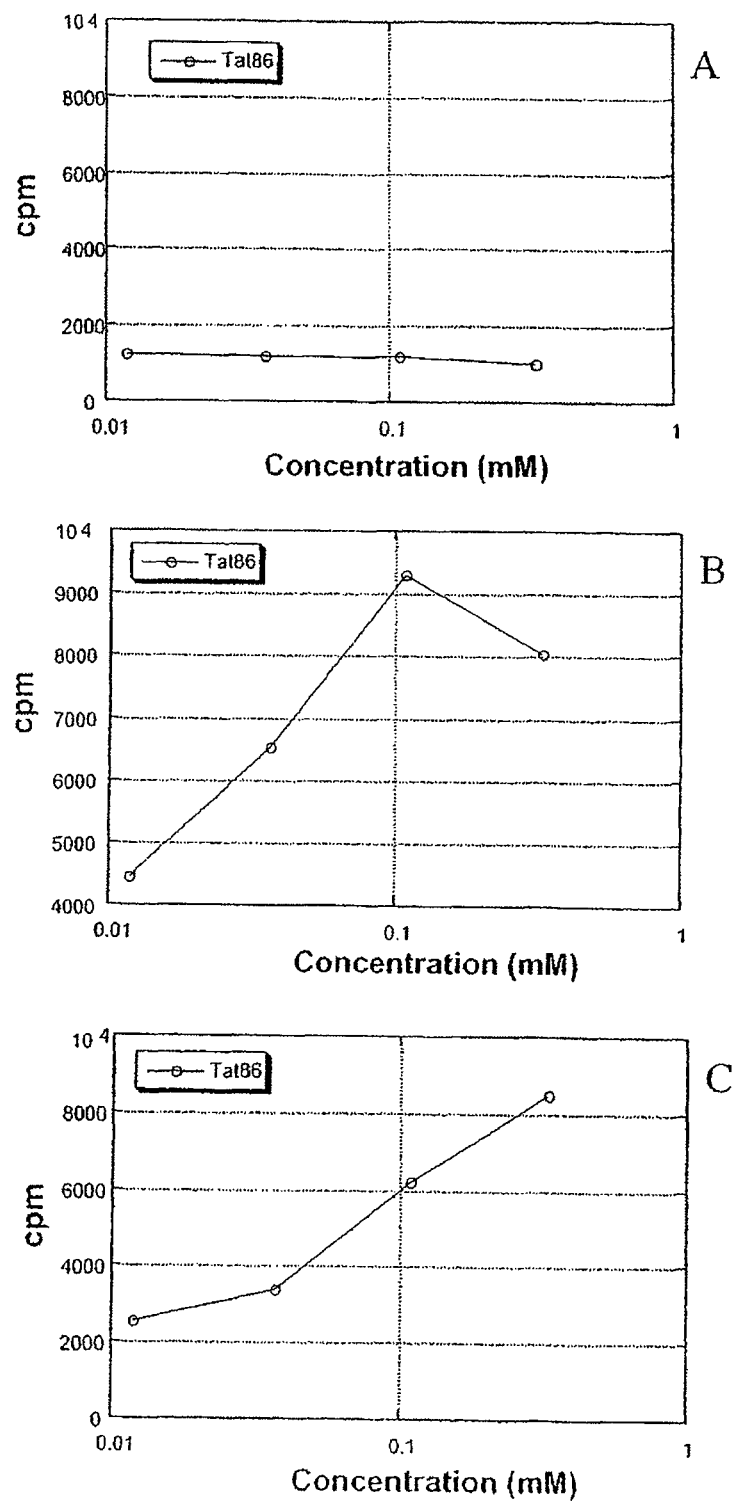
FIG. 14 illustrates the cellular response induced by immunization with Tat86 (A), Tat86C(22-37)StBu (B) and Tat86C(22-37)StBu/Hep6000 (C). The incorporation of triturated thymidine by the immunized mouse splenocytes was measured after stimulation with increasing concentrations of Tat (0.01 to 0.5 µM), FIGS. 15 (A, B and C) illustrate the decrease in transactivating capacity of the Tat derivatives. Hela cells transfected with a reporter plasmid containing the GFP gene under the transcriptional control of the HIV-1 LTR were incubated in the presence of chloroquine and of Tat or of Tat derivatives.

Similar experiments, carried out in SWISS mice and in the absence of adjuvant, show that the combination of the two modifications also makes it possible to obtain an increase in immunogenicity greater than that obtained with just one of these modifications, in an outbred population, and in the absence of adjuvant (FIG. 13).

e) The Tat86C(22-37)StBu Derivative, Free or Complexed with Heparin, Induces T Cells in the Animal While the anti-Tat antibody response plays an essential role in limiting the progression of the disease, the cellular response directed against Tat also has an important place in the protection with respect to viral infection. For this reason, the effect of the highly immunogenic derivatives of Tat on the anti-Tat cellular response was evaluated. The results illustrated in FIG. 14 show that the splenocytes of mice immunized with Tat86 do not proliferate in vitro in the presence of Tat, which indicates that the immunization with the wild-type form of Tat86 does not make it possible to induce specific T cells in the animal (FIG. 14A). On the other hand, the splenocytes derived from the immunizations with Tat86C(22-37) StBu (FIG. 14B) and Tat86C(22-37)StBu/Hep6000 (FIG. 14C) proliferate "in vitro" in the presence of Tat86, which indicates that T cells are clearly activated by immunization using these two immunogens.

EXAMPLE 5

Analysis of the Transactivating Properties of the Tat Derivatives

1) Materials and Methods

A reporter plasmid, called pLTR-G, comprising the gene of the green fluorescent protein EGFP under the transcriptional control of the HIV-1 LTR, was constructed and stabily transfected into Hela cells.

More specifically, the sequence of the LTR of the AVR-2 isolate of HIV-1 (Jones et al., Curr. Opin, Cell. Biol., 1993, 5: 461-468 and GenBank accession number K02007) covering positions −137 to +58, relative to the transcription initiation site, was synthesized according to the method described in Stemmer et al., Gene, 1995, 164: 49-53. The synthetic LTR thus obtained was digested with HindIII and SacII and cloned at the same sites of the plasmid pEGFP-1 (Clontech), upstream of the EGFP gene devoid of promoter, to give the plasmid pLTR-G.

A Hela cell line stably transfected with the plasmid pLTR-G, and expressing EGFP in an activatable manner in the presence of Tat, was selected.

The line of Hela cells transfected with the reporter plasmid was incubated in the presence of Tat or of Tat derivatives prepared as described in Example 1, and of chloroquine (final concentration of 100 µM), in a serum-free medium. After incubation for 3 hours at 37° C., DMEM medium containing 10% fetal calf serum was added. The cells were then incubated for 45 hours at 37° C. and the cellular fluorescence was analyzed by flow cytometry.

2) Results

Figure 15:
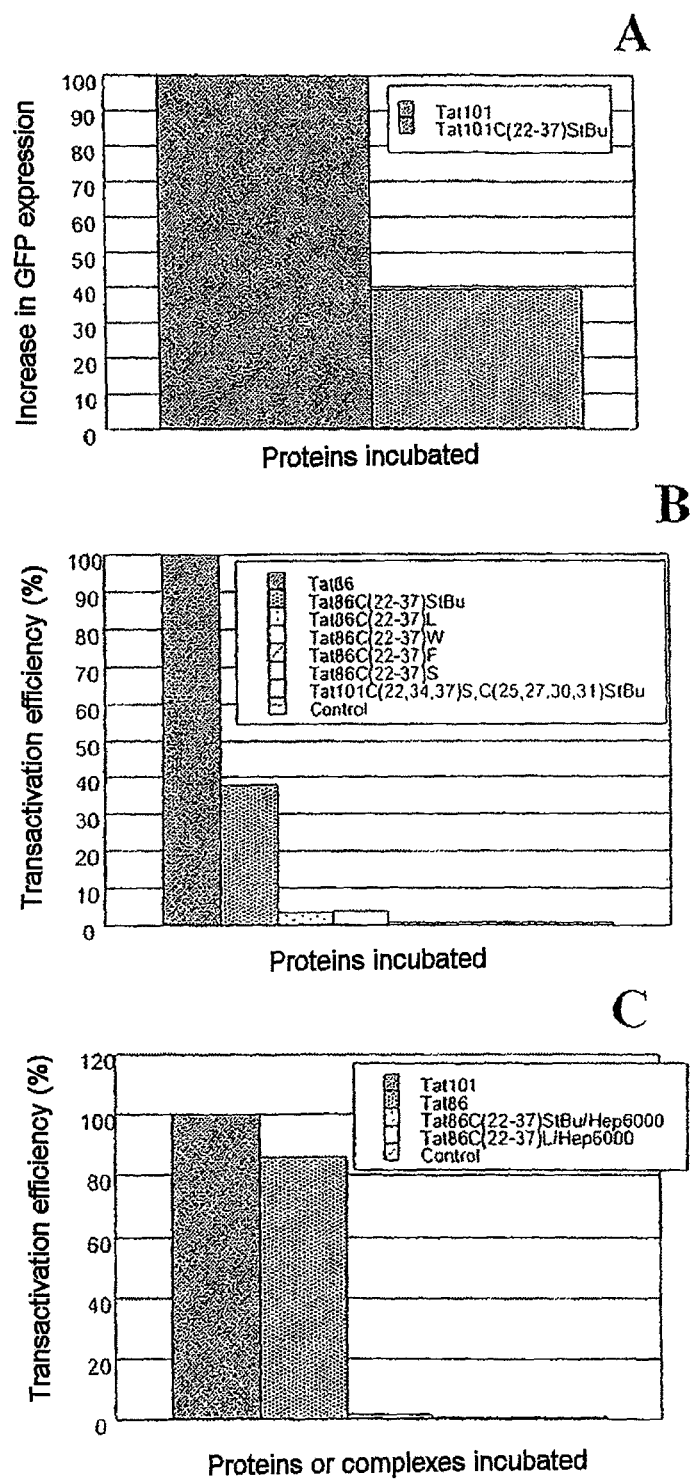

FIG. 15 shows that, contrary to Tat101 and Tat86 which are capable of transactivating the HIV LTR, the Tat derivatives have a reduced transactivation activity. With the exception of the derivatives Tat101C(22-37)StBu and Tat86C(22-37) StBu, the transactivation activity of which is reduced only by 60% compared with that of Tat101 or Tat86, all the other derivatives have a transactivating capacity which is virtually abolished (reduced by 95% to 99% compared with Tat101 or Tat86).

EXAMPLE 6

Measurement of the Resistance of Tat and of its Derivatives with Respect to Proteolytic Degradation The proteolytic stability of Tat and of its derivatives were studied by analysis of the persistence of a B epitope (KGLGI-SYGRK) of the core region, which is recognized by the monoclonal antibody called anti-Tat17S, and is particularly sensitive to chymotrypsin, due to the fact that it contains three hydrophobic residues (L, I and Y). The core region was selected for the following reasons: (i) it is not modified in all the Tat derivatives studied, (ii) it is not involved in the binding with heparin-type ligands (Example 3), and (iii) it is not modified in the hydrophobic derivatives of Tat (Example 4).

1) Materials and Methods

Tat and its derivatives are dissolved in a 50 mM phosphate buffer, pH 7. 2.5 µg of Tat or one of its derivatives are incubated in the presence of phosphate buffer alone or of phosphate buffer containing chymotrypsin in an enzyme/substrate ratio of 1/50 (W/W). After 2 hours at 37° C., the reaction is stopped by adding PMSF (final concentration 5 mM). 300 μl of phosphate buffer, pH 7, are then added and serial dilutions of the reaction medium are distributed into the wells of an ELISA plate. After incubation overnight at 4° C., the plates are saturated by adding 200 μl of 100 mM sodium phosphate buffer, pH 7.2, containing 0.3% bovine serum albumin and 0.003% thymerosal. After incubation for one hour at 37° C., the plates are washed in 0.01M sodium phosphate buffer, pH 7.2, containing 0.05% tween 20. An ascites fluid containing the anti-Tat17S monoclonal antibody specific for the core region of Tat is incubated at 1/100 in the wells of the ELISA plates. After incubation at ambient temperature for 2 hours, the plates are washed in the same buffer as previously, and a peroxydase-coupled anti-mouse immunoglobulin goat polyclonal antibody is added (dilution 1/5000). After incubation at ambient temperature for 30 minutes, the plates are washed in the same buffer as previously, and ABTS is added to the wells. After incubation at ambient temperature for 30 minutes, the absorbance at 414 nm is measured using an automatic reader (Multiskan MCC340, Titertek).

The proportion of Tat that has resisted the action of the chymotrypsin is established as being the ratio of the dilution of Tat in the presence of chymotrypsin (Tat chymo) to the dilution of Tat in the absence of chymotrypsin (Tat in phosphate buffer: Tat bf). This ratio is measured for an optical density equal to 1 after incubation of the various antibodies and of the substrate. This ratio is measured for all the Tat derivatives (Tat derivative chymo/Tat derivative bf). The stability of the derivative compared with wild-type Tat is then determined by dividing the ratio obtained for each Tat derivative by the ratio measured for wild-type Tat, and multiplying the result by 100 ((Tat derivative chymo/Tat derivative bf)/(wild-type Tat chymo/wild-type Tat bf)×100). A percentage greater than 120% corresponds to an increase in stability compared with wild-type Tat (value equal to 100%).

2) Results

The sensitivity of the Tat derivatives to proteolytic degradation is presented in Tables I and II below:

TABLE I

Stability of the Tat derivatives with respect to chymotrypsin digestion (Assay No. 1)

| Tat derivatives | Stability compared with Tat101 or Tat86 |
|---|---|
| Tat86C(22-37)S | 49% |
| Tat86C(22-37)StBu | 156% |
| Tat86C(22-37)L | 194% |
| Tat86C(22-37)F | 210% |
| Tat86C(22-37)W | 310% |
| Tat86/Hep6000 | 430% |
| Tat86/Zn | 167% |
| Tat101C(22-37)StBu | 132% |
| Tat10C(22,34,37)S,C(25,27,30,31)StBu | 755% |
| Tat101/Hep6000 | 833% |

TABLE II

Stability of the Tat derivatives with respect to chymotrypsin digestion (Assay No. 2)

| Tat derivatives | Stability compared with Tat101 or Tat101R(52,53)Q |
|---|---|
| Tat101/Zn | 216% |
| Tat101/Zn/Hep6000 | 191% |
| Tat101/PPS | 1110% |
| Tat101/Dextran | 330% |
| Tat101R(52,53)Q/Hep6000 | 390% |
| Tat101R(52,53)Q/Zn/Hep6000 | 164% |

Tables I and II indicate that the complexation of Tat with a ligand such as a polysulfated sugar (heparin, dextran sulfate, pentosan polysulfate) or a metal ion, in particular a divalent cation such as $Zn^{2+}$, or else the increase in the hydrophobic nature of Tat increase the stability of Tat, as shown by the increased resistance of the Tat derivatives according to the invention with respect to proteolytic degradation. By comparison, the control derivative, Tat86Ser, which is substituted with polar amino acids, is less stable than Tat86.

EXAMPLE 7

Comparative Analysis of the Antibody Response Induced by Tat Complexed with Various Ligands 1) Materials and Methods a) Production of Tat/Ligand Complexes The Tat101 protein and the inactivated derivative Tat101R(52,53)Q, free or complexed with heparin, with dextran sulfate, with pentosan polysulfate or else with $Zn^{2+}$ ions, are produced as described in Example 1.

b) Analysis of the Antibody Response Induced by Tat and the Tat/Ligand Complexes, in the Animal The analysis of the antibody response induced by Tat101 and the Tat101/Dextran and Tat101/PPS complexes was carried out in the BALB/c mouse. The various immunogens were mixed at equal volume with alumina hydroxide and then injected intraperitoneally at a rate of 5 μg of Tat protein per BALB/c mouse, in a final volume of 100 μl. A blood sample was taken 14 and 28 days after immunization.

Alternatively, BALB/c mice were immunized with Tat101 or the inactivated derivative Tat101R(52,53)Q, free or complexed with $Zn^{2+}$ and/or with heparin, in the absence of adjuvant, subcutaneously, at a rate of 5 μg of Tat protein per mouse, in a final volume of 100 μl. The mice were immunized twice, 14 days apart. A blood sample was taken 14 days after the second immunization. The sera were then tested for the presence of anti-Tat antibodies by means of an immunoenzymatic assay (ELISA) as described in Example 3.

2) Results

Figure 16:
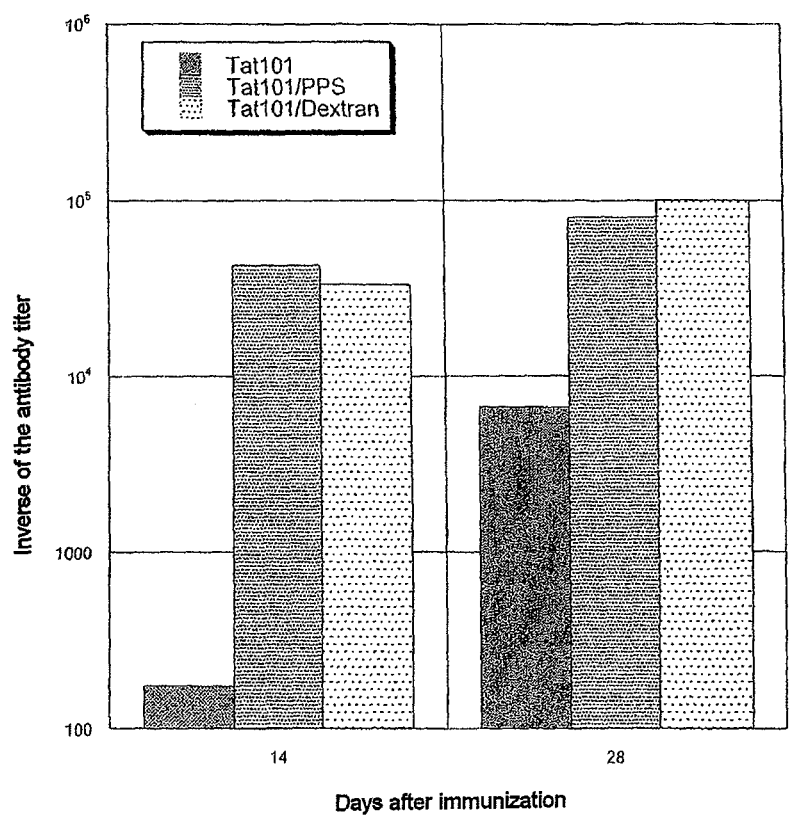
FIG. 16 illustrates the comparative analysis by ELISA of the immunogenicity of Tat101, Tat101/PPS and Tat101/dextran, in BALB/c mice. The values indicated correspond to the inverse of the antibody titer, measured 14 days and 28 days after a single immunization in the presence of alumina hydroxide.

The anti-Tat antibody response induced by immunization of BALB/c mice with either Tat101 mixed with alumina hydroxide, or TAT101/Dextran or Tat101/PPS complexes, mixed with alumina hydroxide, was analyzed by ELISA. The results show that the humoral response is increased when Tat101 is complexed beforehand with a polysulfated sugar (FIG. 16); the antibody titers induced with Tat101 are ten times lower than those induced with Tat101/Dextran or Tat101/PPS. The results are comparable to those obtained with the Tat/Hep6000 and Tat/Hep15 000 complexes (Example 3 and FIG. 4).

Figure 17:
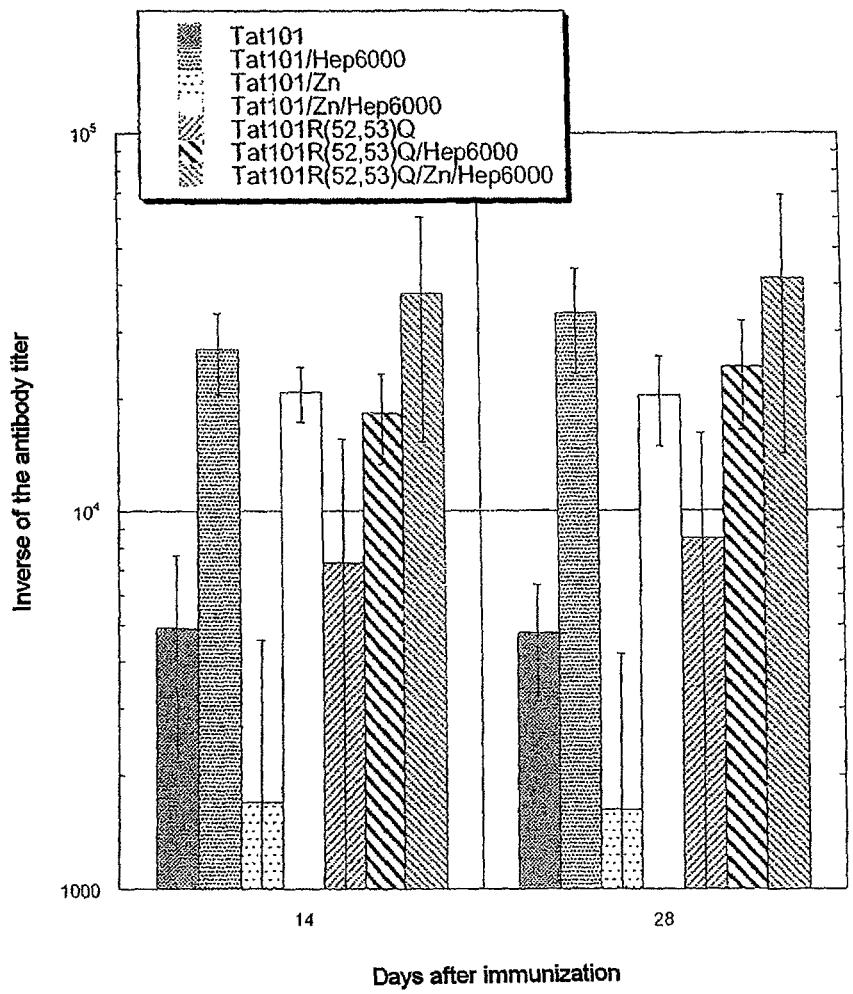
FIG. 17 illustrates the comparative analysis by ELISA of the immunogenicity, in the absence of adjuvant, of Tat101 and of an inactivated derivative (Tat101R(52,53)Q), complexed with $Zn^{2+}$ and/or with heparin, or noncomplexed, in SWISS mice. The values indicated correspond to the inverse of the antibody titer, measured 14 days and 28 days after the last immunization.

The anti-Tat antibody response induced by immunization of BALB/c mice with Tat101 or the inactivated derivative Tat101R(52,53)Q, free or complexed with $Zn^{2+}$ and/or with heparin, and in the absence of adjuvant, show that, unlike the Tat/heparin complexes (Tat101/Hep6000), the Tat/Zn complexes are not capable of inducing an increase in the immune response, in the absence of adjuvant (FIG. 17). On the other hand, the Tat/heparin/Zn complexes behave like the Tat/heparin complexes and are capable of inducing an increase in the immune response, in the absence of adjuvant. Tat101 and the inactivated derivative of Tat (Tat101R(52,53)Q) give comparable results.

EXAMPLE 8

Analysis of the Tat Forms Stabilized Using $Zn^{2+}$

1) Methods
a) Electrophoretic Analysis of the Tat Forms

The Tat101 protein (final concentration 58 μM), prepared as described in Example 1, was incubated in PBS buffer (pH 7.4), in the presence of $ZnCl_2$ (in a 6-fold excess relative to the Tat cysteines) or in the absence of $ZnCl_2$, for various periods of time, at ambient temperature, without stirring, in the dark.

The appearance of the oligomeric forms of Tat was analyzed by electrophoresis on a gel consisting of a non-crosslinked polymer forming dynamic pores, and analysis on a bioanalyzer (Agilent 2100, Agilent Technologies), using the protein 50 Plus LabChip kit (Agilent Technologies). The chips were prepared according to the protocol provided by the manufacturer; the channels of the chip were filled with the mixture of gel and fluorescent marker used for detecting the proteins.

The samples of Tat101 incubated in PBS, in the presence or absence of $ZnCl_2$, were preincubated with maleimide (20 mM), so as to block the reactive cysteines and prevent the formation of disulfide bridges during the denaturation or the migration of the samples in the gel.

The Tat samples were then denatured in the presence of SDS, at 95° C. for 7 minutes, before they were loaded onto the chip. The chip was then loaded onto the bioanalyzer and each sample was separated in the separating channel and detected by measuring the fluorescence (670 nm-700 nm) in 45 seconds.

b) Analysis of the Transactivation Capacity of the Tat Forms

The experimental protocol is that described in Example 5.

Figure 18:
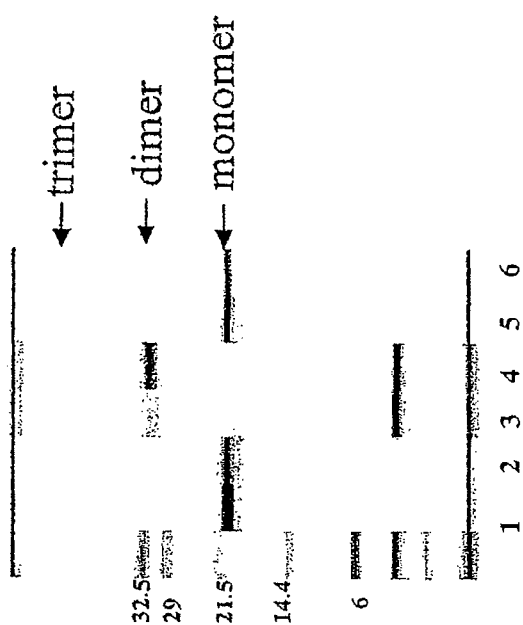
FIG. 18 illustrates the analysis, by electrophoresis using a noncrosslinked gel, of the effect of $Zn^{2+}$ on the appearance of the oligomeric forms of Tat. Tat101 (final concentration of 58 µm) was incubated in PBS buffer (pH 7.4), in the presence of $ZnCl_2$ (in 6-fold excess relative to the Tat cysteines) or in the absence of $ZnCl_2$, for various times (T), at ambient temperature, without agitation, in the dark. At the end of the incubation, the samples were treated with maleimide (20 mM), in such a way as to block the reactive cysteines and avoid the formation of disulfide bridges during the denaturation or the migration of the samples in the gel. The samples were then denatured in the presence of SDS, at 95° C., for 7 minutes before they were loaded onto the gel. Tat101 incubated in the absence of $ZnCl_2$ (Lane 1: T=0 min; Lane 2: T=1 hour; Lane 3: T=24 hours; Lane 4: T=5 days). Tat101 incubated in the presence of $ZnCl_2$ (Lane 5: T=1 hour; Lane 6: T=5 days)
Figure 19:
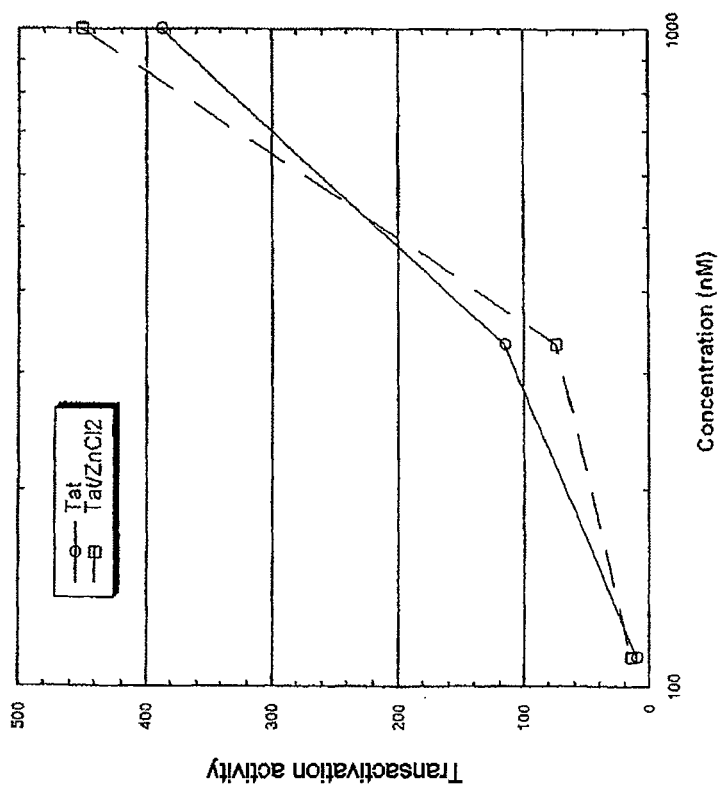
FIG. 19 illustrates the absence of effect on the transactivating capacity of Tat, of the stabilization of Tat with $Zn^{2+}$. Hela cells transfected with a reporter plasmid containing the GFP gene under the transcriptional control of the HIV-1 LTR were incubated in the presence of chloroquine and of various concentrations of Tat (nM), preincubated with $ZnCl_2$, or not preincubated with $ZnCl_2$, and then the cellular fluorescence was analyzed by flow cytometry.

2) Results
a) Electrophoretic Analysis of the Tat Forms Stabilized Using $Zn^{2+}$ The electrophoretic analysis of Tat (FIG. 18) shows that Tat is an unstable molecule which evolves over time so as to form dimers or trimers. After incubation for 5 days (lane 4), two bands corresponding to oligomeric forms are predominantly found. The first is predominant and corresponds to dimeric forms, whereas the second corresponds to trimeric forms. The monomeric form which can be observed in lanes 1, 2 and 3, has, for its part, virtually disappeared. On the other hand, in the presence of $ZnCl_2$, only one band is found, corresponding to the monomeric form of Tat (lane 6). The zinc, which can bring about the formation of non-covalent homo- or heterodimers, therefore stabilizes Tat by blocking the formation of intermolecular disulfide bridges mediated by the cysteines.

b) Analysis of the Transactivation Capacity of the Tat Forms Stabilized Using $Zn^{2+}$ The transactivating capacity of Tat in the presence or absence of $ZnCl_2$ was analyzed in order to evaluate whether the stabilization with zinc impairs the biological activity of Tat. FIG. 19 shows that the cells transfected with the reporter plasmid emit fluorescence for concentrations of Tat or of Tat diluted beforehand with $ZnCl_2$ which are similar, which indicates that the zinc stabilizes Tat without disturbing its main biological activity.

As emerges from the above, the invention is in no way limited to those of its methods of implementation, execution and application that have just been more specifically described; on the contrary, it encompasses all the variants thereof that may occur to a person skilled in the art, without departing from either the context or the scope of the present invention.

The invention claimed is:

1. An HIV immunogenic composition formulated for administration to a subject, comprising at least one isolated Tat antigen and a pharmaceutically acceptable vehicle, wherein the isolated Tat antigen is a stabilized Tat antigen resistant to proteolytic degradation selected from the group consisting of:
   a) a Tat/ligand complex comprising at least an inactivated HIV Tat protein or an inactivated Tat fragment capable of inducing an anti-Tat specific humoral and/or cellular immune response in humans, and a polysulfated sugar, wherein said inactivated Tat protein or said inactivated Tat fragment comprises the substitution of each of the cysteines at positions 22, 34 and 37 to serine or else the substitution of each of the arginines at positions 52 and 53 to glutamines,
   b) an artificial variant of an inactivated HIV Tat protein or of an inactivated Tat fragment capable of inducing an anti-Tat specific humoral and/or cellular immune response in humans, wherein the seven cysteines located at positions 22, 25, 27, 30, 31, 34 and 37 of the Tat amino acid sequence are modified with the hydrophobic group S-tert-butyl or substituted with a hydrophobic amino acid chosen from: Leucine, Isoleucine, Phenylalanine, Tryptophan and Tyrosine, and each of the arginines at positions 52 and 53 is substituted with a glutamine,
   c) an artificial variant of an inactivated HIV Tat protein or of an inactivated Tat fragment capable of inducing an anti-Tat specific humoral and/or cellular immune response in humans, wherein the cysteines located at positions 22, 34 and 37 of the Tat amino acid sequence are substituted with a serine and the cysteines located at positions 25, 27, 30 and 31 of said sequence are modified with the hydrophobic group S-tert-butyl, and
   d) a complex between the artificial variant of the inactivated Tat protein or of the inactivated Tat fragment defined in b) or c), and a polysulfated sugar.

2. The immunogenic composition as claimed in claim 1, characterized in that said polysulfated sugar is chosen from: dextran sulfate, pentosan polysulfate, and polysulfated glycosaminoglycans, including heparin or heparan sulfate.

3. The immunogenic composition as claimed in claim 1, characterized in that said polysulfated sugar is a heparin having a molecular weight of 15000 Da or a heparin fragment having a molecular weight of 6000 Da.

4. An HIV immunogenic composition comprising at least one isolated Tat antigen, wherein the isolated Tat antigen is a stabilized Tat antigen resistant to proteolytic degradation, wherein the stabilized Tat antigen derives from an inactivated Tat protein or from an inactivated Tat fragment, and wherein said inactivated Tat protein or said inactivated Tat fragment comprises the substitution of each of the cysteines at positions 22, 34 and 37 to serines or else the substitution of each of the arginines at positions 52 and 53 to glutamines.

5. The immunogenic composition as claimed in claim 1, characterized in that said inactivated Tat protein or said inactivated Tat fragment in a) is also complexed with a metal ion.

6. The immunogenic composition as claimed in claim 1, characterized in that said artificial variant of an inactivated Tat protein or of an inactivated Tat fragment in b), c) or d) is also complexed with a metal ion.

7. The immunogenic composition as claimed in claim 1, characterized in that said inactivated Tat protein or said inactivated Tat fragment is monomer.

8. The immunogenic composition as claimed in claim 1, characterized in that said inactivated Tat protein or said inactivated Tat fragment is an oligomer.

9. The immunogenic composition as claimed in claim 8, characterized in that said oligomer is formed from the covalent association of said inactivated Tat protein and/or said inactivated Tat fragment by means of an intermolecular disulfide bond involving one of the cysteines at position 22, 25, 27, 30, 31, 34 or 37.

10. The immunogenic composition as claimed in claim 9, characterized in that said disulfide bond involves one of the cysteines at positions 22, 34 and 37.

11. An HIV immunogenic composition comprising at least one isolated Tat antigen, wherein the isolated Tat antigen is a stabilized Tat antigen resistant to proteolytic degradation, wherein the stabilized Tat antigen is an artificial variant, characterized in that the stabilized Tat antigen is a dimer formed from the association, by means of a disulfide bridge between the cysteines at position 34, of two Tat proteins or of two Tat fragments capable of inducing an anti-Tat specific humoral and/or cellular immune response in humans, which comprise a serine at positions 22 and 37 and a leucine at positions 25, 27, 30 and 31.

12. The immunogenic composition as claimed in claim 8, characterized in that said oligomer is formed from the non-covalent association of said inactivated Tat protein and/or said inactivated Tat fragment by means of metal ions.

13. The immunogenic composition as claimed in claim 1, characterized in that it further comprises an adjuvant.

14. The immunogenic composition as claimed in claim 1, characterized in that it consists of said stabilized antigen and a pharmaceutically acceptable vehicle.

15. The immunogenic composition as claimed in claim 13, characterized in that said adjuvant is alumina hydroxide.

16. The immunogenic composition as claimed in claim 5, characterized in that said metal ion is a polyvalent cation.

17. The immunogenic composition as claimed in claim 5, characterized in that said metal ion is a divalent cation.

18. The immunogenic composition as claimed in claim 5, characterized in that said metal ion is $Zn^{2+}$ or $Cd^{2+}$.

19. The immunogenic composition as claimed in claim 6, characterized in that said metal ion is a polyvalent cation.

20. The immunogenic composition as claimed in claim 6, characterized in that said metal ion is a divalent cation.

21. The immunogenic composition as claimed in claim 6, characterized in that said metal ion is $Zn^{2+}$ or $Cd^{2+}$.

22. The immunogenic composition as claimed in claim 8, characterized in that said oligomer is a dimer.

23. The immunogenic composition as claimed in claim 9, characterized in that said oligomer is a dimer.

24. The immunogenic composition as claimed in claim 12, characterized in that said oligomer is a dimer.

25. The immunogenic composition as claimed in claim 12, characterized in that said metal ions are polyvalent cations.

26. The immunogenic composition as claimed in claim 12, characterized in that said metal ions are divalent cations.

27. The immunogenic composition as claimed in claim 12, characterized in that said metal ions are $Zn^{2+}$ or $Cd^{2+}$ ions.

28. The immunogenic composition as claimed in claim 1, further comprising a carrier substance.

29. The immunogenic composition as claimed in claim 1, wherein the subject is a human.

\* \* \* \* \*

UNITED STATES PATENT AND TRADEMARK OFFICE
CERTIFICATE OF CORRECTION

| | | |
|---|---|---|
| PATENT NO. | : 8,501,193 B1 | Page 1 of 1 |
| APPLICATION NO. | : 10/599448 | |
| DATED | : August 6, 2013 | |
| INVENTOR(S) | : Pascal Drevet et al. | |

It is certified that error appears in the above-identified patent and that said Letters Patent is hereby corrected as shown below:

In the Claims

In Claim 7, at Column 28, line 27, delete "is monomer"

and replace it with -- is a monomer --.

Signed and Sealed this
Twenty-second Day of October, 2013

Teresa Stanek Rea
*Deputy Director of the United States Patent and Trademark Office*

SEQUENCE LISTING

```
<160> NUMBER OF SEQ ID NOS: 4

<210> SEQ ID NO 1
<211> LENGTH: 101
<212> TYPE: PRT
<213> ORGANISM: Human immunodeficiency virus
<220> FEATURE:
<223> OTHER INFORMATION: Tat protein

<400> SEQUENCE: 1

Met Glu Pro Val Asp Pro Lys Leu Glu Pro Trp Lys His Pro Gly Ser
1               5                   10                  15

Gln Pro Lys Thr Ala Cys Asn Asn Cys Tyr Cys Lys Lys Cys Cys Phe
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Ser Lys Gln Pro Ala Ser Gln Pro Arg Gly Asp
65                  70                  75                  80

Pro Thr Gly Pro Lys Glu Ser Lys Lys Val Glu Arg Glu Thr Glu
                85                  90                  95
```

```
Thr Asp Pro Val Asp
            100

<210> SEQ ID NO 2
<211> LENGTH: 86
<212> TYPE: PRT
<213> ORGANISM: Human immunodeficiency virus
<220> FEATURE:
<223> OTHER INFORMATION: Tat protein

<400> SEQUENCE: 2

Met Glu Pro Val Asp Pro Lys Leu Glu Pro Trp Lys His Pro Gly Ser
1               5                   10                  15

Gln Pro Lys Thr Ala Cys Asn Asn Cys Tyr Cys Lys Lys Cys Cys Phe
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Ser Lys Gln Pro Ala Ser Gln Pro Arg Gly Asp
65                  70                  75                  80

Pro Thr Gly Pro Lys Glu
                85

<210> SEQ ID NO 3
<211> LENGTH: 86
<212> TYPE: PRT
<213> ORGANISM: Human immunodeficiency virus
<220> FEATURE:
<223> OTHER INFORMATION: Tat protein

<400> SEQUENCE: 3

Met Glu Pro Val Asp Pro Lys Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 4
<211> LENGTH: 101
<212> TYPE: PRT
<213> ORGANISM: Human immunodeficiency virus
<220> FEATURE:
<223> OTHER INFORMATION: Tat protein
<220> FEATURE:
<221> NAME/KEY: MISC_FEATURE
<222> LOCATION: (1)..(1)
<223> OTHER INFORMATION: Xaa. Norleucine

<400> SEQUENCE: 4

Xaa Glu Pro Val Asp Pro Lys Leu Glu Pro Trp Lys His Pro Gly Ser
1               5                   10                  15

Gln Pro Lys Thr Ala Cys Asn Asn Cys Tyr Cys Lys Lys Cys Cys Phe
            20                  25                  30

His Cys Gln Val Cys Phe Thr Lys Lys Gly Leu Gly Ile Ser Tyr Gly
```

```
                    35                  40                  45
Arg Lys Lys Arg Arg Gln Arg Arg Ala Pro Gln Asp Ser Gln Thr
    50                  55                  60

His Gln Val Ser Leu Ser Lys Gln Pro Ala Ser Gln Pro Arg Gly Asp
65                      70                  75                  80

Pro Thr Gly Pro Lys Glu Ser Lys Lys Lys Val Glu Arg Glu Thr Glu
                85                  90                  95

Thr Asp Pro Val Asp
            100
```